(12) United States Patent
Arya et al.

(10) Patent No.: US 10,765,694 B2
(45) Date of Patent: Sep. 8, 2020

(54) COMPOSITIONS AND METHODS FOR DELIVERING INHIBITORY OLIGONUCLEOTIDES

(71) Applicant: The United States of America, as represented by the Secretary, Department of Health & Human Services, Rockville, MD (US)

(72) Inventors: Bira Arya, Elliott City, MD (US); Purevdorj Olkhanud, Baltimore, MD (US); Juan Espinoza, Los Angeles, CA (US)

(73) Assignee: The United States of America, as represented by the Secretary, Department of Health and Human Services, Rockville, MD (US)

( * ) Notice: Subject to any disclaimer, the term of this patent is extended or adjusted under 35 U.S.C. 154(b) by 0 days.

(21) Appl. No.: 15/204,789

(22) Filed: Jul. 7, 2016

(65) Prior Publication Data
US 2016/0310609 A1 Oct. 27, 2016

Related U.S. Application Data

(60) Division of application No. 14/220,726, filed on Mar. 20, 2014, now Pat. No. 9,415,116, which is a continuation of application No. 12/988,148, filed as application No. PCT/US2009/040607 on Apr. 15, 2009, now Pat. No. 8,703,921.

(60) Provisional application No. 61/045,088, filed on Apr. 15, 2008.

(51) Int. Cl.
| | |
|---|---|
| A61K 39/00 | (2006.01) |
| A61K 31/713 | (2006.01) |
| C12N 15/87 | (2006.01) |
| A61K 47/64 | (2017.01) |
| C07K 14/005 | (2006.01) |
| C07K 14/52 | (2006.01) |

(52) U.S. Cl.
CPC .......... *A61K 31/713* (2013.01); *A61K 47/642* (2017.08); *A61K 47/6455* (2017.08); *C07K 14/005* (2013.01); *C07K 14/523* (2013.01); *C12N 15/87* (2013.01); *C07K 2319/33* (2013.01); *C07K 2319/74* (2013.01); *C07K 2319/85* (2013.01)

(58) Field of Classification Search
None
See application file for complete search history.

(56) References Cited

U.S. PATENT DOCUMENTS

| | | | |
|---|---|---|---|
| 5,108,921 A | 4/1992 | Low et al. | |
| 5,416,016 A | 5/1995 | Low et al. | |
| 5,514,548 A | 5/1996 | Krebber et al. | |
| 5,849,902 A | 12/1998 | Woolf et al. | |
| 5,898,031 A | 4/1999 | Crooke | |
| 6,107,094 A | 8/2000 | Crooke | |
| 6,172,208 B1 | 1/2001 | Cook | |
| 6,294,353 B1 | 9/2001 | Pack et al. | |
| 6,335,434 B1 | 1/2002 | Guzaev et al. | |
| 6,653,068 B2 | 11/2003 | Frisch et al. | |
| 6,667,150 B1 | 12/2003 | Rudert et al. | |
| 6,692,935 B1 | 2/2004 | Pack et al. | |
| 6,696,245 B2 | 2/2004 | Winter et al. | |
| 6,753,136 B2 | 6/2004 | Lohning | |
| 8,703,921 B2 | 4/2014 | Arya | |
| 9,415,116 B2 | 8/2016 | Arya | |
| 2004/0058886 A1 | 3/2004 | Scaringe | |
| 2007/0042983 A1 | 2/2007 | Haeberli et al. | |
| 2007/0231392 A1 | 10/2007 | Wagner et al. | |
| 2014/0377179 A1 | 12/2014 | Arya | |

FOREIGN PATENT DOCUMENTS

| | | |
|---|---|---|
| WO | WO 00/53722 | 9/2000 |
| WO | WO 2004/110375 | 12/2004 |
| WO | WO 2006/023491 | 3/2006 |
| WO | WO 2007/041364 | 4/2007 |
| WO | WO 2007/127219 | 11/2007 |
| WO | WO 2008/092081 | 7/2008 |

OTHER PUBLICATIONS

Loetscher et al (FASEB Journal, 1994. vol. 8, pp. 1055-1060).*
Matsuda et al (Journal of Virology, 1988. vol. 62, No. 9, pp. 3517-3521).*
Liu et al (Eur. J. Immunol. 2004. vol. 34. pp. 1680-1687).*
AAU93921. Jul. 2, 2002. Birkett from WO200214478.*
Adah et al., "Chemistry and biochemistry of 2',5'-oligoadenylate-based antisense strategy", Curr. Med. Chem., 8, 1189-1212 (2001).
Bahramian, et al., " Transcriptional and posttranscriptional silencing of rodent α1(I) collagen by a homologous Transcriptionally self-silenced transgene", Molecular and Cellular Biology 19:274-283 (1999).
Bass, "The short answer", Nature, 411, 428-429 (2001).
Benton, et al., "Screening λgt recombinant clones by hybridization to single plaques in situ", Science 196:180-182 (1977).

(Continued)

*Primary Examiner* — Celine X Qian
(74) *Attorney, Agent, or Firm* — Locke Lord LLP; Nicholas J. DiCeglie, Jr.

(57) ABSTRACT

The present invention features compositions and methods that make use of complexes comprising one or more inhibitory nucleic acids and a targeting polypeptide, wherein the targeting polypeptide consists of a cell surface receptor ligand. The compositions can be used in methods of silencing gene expression in a cell, delivering agents to a target cell, and in treating or preventing a disease or disorder in a subject.

18 Claims, 8 Drawing Sheets
Specification includes a Sequence Listing.

(56) References Cited

OTHER PUBLICATIONS

Caron et al., "Human FGF-1 gene transfer promotes the formation of collateral vessels and arterioles in ischemic muscles of hypercholesterolemic hamsters", J. Gene Medicine 6:1033-1045 (2004).

Chiu, et al., "Inhibition of human immunodeficiency virus type 1 replication by RNA interference directed against human transcription elongation factor P-TEFb (CDK9/CyclinT1)", J. Virology, 78:2517-2529 (2004).

Clemens et al., "The double-stranded RNA-dependent protein kinase PKR: structure and function", J. Interferon & Cytokine Res., 17, 503-524 (1997).

Conry, et al., "Phase I trial of a recombinant vaccinia virus encoding carcinoembryonic antigen in metastatic adenocarcinoma: comparison of intradermal versus subcutaneous administration", Clin. Cancer Res. 5:2330-2337 (1999).

Crooke, "Advances in understanding the pharmacological properties of antisense oligonucleotides" Ad. Pharmacol., 40, 1-49 (1997).

Crooke, "Antisense therapeutics" Biotech. Genet. Eng. Rev., 15, 121-157 (1998).

Crooke, "Progress in antisense technology: the end of the beginning", Methods Enzymol., 313, 3-45 (2000).

Delihas et al., "Natural antisense RNA/target RNA interactions: possible models for antisense oligonucleotide drug design", Nature, 15, 751-753 (1997).

Diallo et al., "Long endogenous dsRNAs can induce complete gene silencing in mammalian cells and primary cultures", Oligunucleotides 13:381-392 (2003).

Elbashir, et al., "Duplexes of 21-nucleotide RNAs mediate RNA interference in cultured mammalian cells", Nature 411:494-498 (2001).

Fire et al., "Potent and specific genetic interference by double-stranded RNA in Caenorhabditis elegans", Nature 391:806-811 (1998).

Fire et al., "RNA-triggered gene silencing", Trends Genet., 15, 358-363 (1999).

Godwin et al., "The synthesis of biologically active pteroyloligo-γ-L-glutamates (folic acid conjugates)", J. Biol. Chem., 247, 2266-2271 (1972).

Grunstein, et al., "Colony hybridization: a method for the isolation of cloned DNAs that contain a specific gene", Proc. Natl. Acad. Sci., USA 72:3961-3965 (1975).

Habus et al., "A mild and efficient solid-support synthesis of novel oligonucleotide conjugates", Bioconjugate Chem., 9, 283-291 (1998).

Hamilton et al., "A species of small antisense RNA in post-transcriptional gene silencing in plans", Science 286:950-951 (1999).

Hammond, et al., "An RNA-directed nuclease mediates post-transcriptional gene silencing in *Drosophila* cells", Nature 404:293-296 (2000).

He et al., "Adenoviral Vectors", Curr Protocols Human Genetics, 40:12.4.1-12.4.25 (2004).

Ishiwata, et al., "Physical-chemistry characteristics and biodistribution of poly(ethylene glycol)-coated liposomes using poly(oxyethylene) cholesteryl ether", Chem. Pharm. Bull. 43:1005-1011 (1995).

Jacobs, et al., "Histone proteins inhibit activation of the interferon-induced protein kinase by binding to double-stranded RNA", J. Interferon Research 8:821-830 (1988).

Kimmel, A. R., "Identification and characterization of specific clones: strategy for confirming the validity of presumptive clones", Methods Enzymol. 152:507-511 (1987).

Lasic, et al., "Liposomes revisited", Science 267:1275-1276 (1995).

Lasic, et al., "The "stealth" Liposome: a prototypical biomaterial", Chem. Rev. 95:2601-2627 (1995).

Lin et al., Policing rogue genes, Nature, 402, 128-129 (1999).

Liu, et al., "Cationic liposome-mediated intravenous gene delivery", J. Biol. Chem. 42:24864-24870 (1995).

Miyagishi, et al., "Strategies for generation of an siRNA expression library directed against the human genome", Oligonucleotides, 13:325-333 (2003).

Muratovska, et al., "Conjugate for efficient delivery of short interfering RNA (siRNA) into mammalian cells", FEBS Letters 558 63-68 (2004).

Myers, et al., "Recombinant dicer efficiently converts large dsRNAs into siRNAs suitable for gene silencing", Nature Biotechnology 21:324-328 (2003).

Nomura et al., "Development of an efficient intermediate, alpha-[2-(trimethylsilyl)ethoxy]-2-N-[2-(trimethylsily1)ethoxycarbonyl]folic acid, for the synthesis of folate (γ)-conjugates, and its application to the synthesis of folate-nucleoside conjugates", J. Org. Chem., 65, 5016-5021, (2000).

Oku, et al., "Real-time analysis of liposomal trafficking in tumor-bearing mice by use of positron emission tomography", Biochim. Biophys. Acta 1238:86-90 (1995).

Parrish, et al., "Distinct roles for RDE-1 and RDE-4 during RNA interference in Caenorhabditis elegans", RNA, 7:1397-1402 (2001).

Provost, et al., "Ribonuclease activity and RNA binding of recombinant humas dicer", European Molecular Biology Organization, 21:5864-5874 (2002).

Schmajuk et al., "Antisense oligonucleotides with different backbones; Modification of splicing pathways and efficacy of uptake", J. Biol. Chem., 274, 21783-21789 (1999).

Sharp, "RNAi and double-strand RNA", Genes & Dev., 13:139-141 (1999).

Song et al., "Antibody mediated in vivo delivery of small interfering RNAs via cell-surface receptors", Nature Biotechnology, doi:10.1038/nbt1101 (2005).

Stein et al., "A specificity comparison of four antisense types: Morpholino, 2'-O-Methyl RNA, DNA, and Phosphorothioate DNA", Antisense N. A. Drug Dev., 7, 151-157 (1997).

Stein, et al., "Antisense oligonucleotides as therapeutic agents—is the bullet really magical?", Science 261, 1004-1012 (1993).

Strauss, "Candidate 'gene silencers' found", Science, 286, 886 (1999).

Tabara et al., "The dsRNA binding protein RDE-4 interacts with RDE-1, DCR-1, and a DExH-Box helicase to direct RNAi in C. elegans", Cell, 109:861-871 (2002).

Wahl et al., "Molecular hybridization of immobilized nucleic acids: theoretical concepts and practical considerations", Methods Enzymol. 152:399-407 (1987).

Wianny, et al., "Specific interference with gene function by double-stranded RNA in early mouse development", Nature Cell Biology, 2:70-75 (2000).

E. Song et al., "Antibody mediated in vivo delivery of small interfering RNAs via cell-surface receptors", Nature Biotechnology, 23(6), pp. 709-717 (2005).

J. Rossi et al., "Receptor-Targeted siRNAs", Nature Biotechnology, 23(6), pp. 682-684 (2005).

P. Kumar et al., "Transvascular delivery of small interfering RNA to the cetnral nervous system", Nature, 448(7149), pp. 39-45 (2007).

Gregory Cesarone et al., "Insulin receptor substrate 1 knockdonwn in human MCF7 ER-Fbreast cancer cells by nuclease-resistant IRS1 siRNA conjugated to a disulfide-bridged D-Peptide analogue of insulin-like growth factor 1", Bioconjugate Chemistry, 18(6), pp. 1831-1840 (2007).

Chun-Fang Xia et al., "Intravenous siRNA of brain cancer with receptor targeting and avidin-biotin technology", Pharmaceutical Research, 24(12), pp. 2309-2316 (2007).

Priti Kumar et al., "T cell-specific siRNA delivery suppresses HIV-1 infection in humanized mice", Cell, 134(4), pp. 577-586 (2008).

International Search Report for PCT/US2009/040607, dated Nov. 2, 2010.

International Preliminary Report on Patentability for PCT/US2009/040607, dated Nov. 9, 2010.

Zamore et al., "RNAi: double-stranded RNA directs the ATP-dependent cleavage of mRNA at 21 to 23 nucleotide intervals", Cell, 101, 25-33 (2000).

Zhang, et al., "Human dicer preferentially cleaves dsRNAs at their termini without a requirement for ATP", European Molecular Biology Organization, 21: 5875-5885 (2002).

\* cited by examiner

FIG. 2

SEQ ID NO: 1

ATGGCACGAGGGACCAACGTGGGCCGGGAGTGCTGCCTGGAGTACTTCAAGGGAGCCATTCCCCTTAGAAAGCTGAAGAC
GTGGTACCAGACATCTGAGGACTGCTCCAGGGATGCCATCGTTTTTGTAACTGTGCAGGGCAGGGCCATCTGTTCGGACC
CCAACAACAAGAGAGTGAAGAATGCAGTTAAATACCTGCAAAGCCTTGAGAGGTCTGATGGTGGTGGCTCTGGCGGTGGG
GGTAGCCTCGACCGCTGCCAGAGCCGTTATTACCGCCAGCGCCAACGTTCTCGCCGCCGTCGCCGCAGCCT
CGAGCCGTGGATCCGCAGAAGAGAAACAGAAACTGATCTCAGAAGAGGATCTGGCCCACCACCATCACCATCACTAA

SEQ ID NO: 2

<u>MARGTNVGRECCLEYFKGAIPLRKLKTWYQTSEDCSRDAIVFVTVQGRAICSDPNNKRVKNAVKYLQSLERS
DGGGSGGGGSL</u>
*DRSQSRSYYRQRQRSRRRRRSLER*
<u>GSAEEQKLISEEDLAHHHHHH</u>

FIG. 3

SEQ ID NO: 3

ATGGCACGAGGGACCAACGTGGGCCGGGAGTGCTGCCTGGAGTACTTCAAGGGAGCCATTCCCCTTAGAAAGCTGAAGAC
GTGGTACCAGACATCTGAGGACTGCTCCAGGGATGCCATCGTTTTTGTAACTGTGCAGGGCCAGGGCCATCTGTTCGGACC
CCAACAACAAGAGAGTGAAGAATGCAGTTAAATACCTGCAAAGCCTTGAGAGGTCTGATGGTGGTGGCTCTGGGCGGTGGG
GGTAGCctcgagAGACGACGAGGCAGGtccCCtagAAGAAGAACTCCCTCgCCCTCgcAGACGAAGGTCTCAATCGCCGCG
TCGCAgAAgATCTCAATCTCGGGTCGACCACCaTCACCATCaCTAA

SEQ ID NO: 4

<u>MRGTNVGRECCLEYFKGAIPLRKLKTWYQTSEDCSRDAIVFVTVQGRAICSDPNNKRVKNAVKYLQSIER</u>
<u>SDGGGSGGGGSLE</u>
RRRGRSPRRRTPSPRRRRSQSPRRRRSQSRVD
<u>HHHHH</u>

FIG. 4

SEQ ID NO: 5

SDGGGSGGGGSLE

SEQ ID NO: 6

DGGGSGGGGSL

SEQ ID NO: 7

GGGSGGGG

SEQ ID NO: 8

GGGGSGGGG

FIG. 5

SEQ ID NO: 9

ARGTNVGRECCLEYFKGAIPLRKLKTWYQTSEDCSRDAIVFVTVQGRAICSDPNNKRVKNAVKYLQSLERSDGGGSGGGG
SPGRRRRRSQSRRRRR

SEQ ID NO: 10

SPYSSDTTPCCFAYIARPLPRAHIKEYFYTSGKCSNPAVVFVTRKNRQVCANPEKKWVREYINSLEMSGGGSGGGG
SPGRRRRRSQSRRRRR

SEQ ID NO: 11

EAPDAINAPVTCCYNFTNRKISVQRLASYRRITSSKCPKEAVIFKTIVAKEICADPKQKWVQDSMDHLDKQTQPKTGGGGSGGGG
SPGRRRRRSQSRRRRR

COMPOSITIONS AND METHODS FOR DELIVERING INHIBITORY OLIGONUCLEOTIDES

RELATED APPLICATIONS/PATENTS & INCORPORATION BY REFERENCE

This application is a divisional application of U.S. patent application Ser. No. 14/220,726, filed on Mar. 20, 2014, which is a continuation application of U.S. patent application Ser. No. 12/988,148, filed Mar. 8, 2011, which is a 35 U.S.C. § 371 U.S. national entry of International Application PCT/US2009/040607 (WO 2009/129281) having an International filing date of Apr. 15, 2009, which claims the benefit of U.S. Provisional Application No. 61/045,088, filed on Apr. 15, 2008. The entire contents of the aforementioned applications are hereby incorporated herein by reference.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. More generally, documents or references are cited in this text, either in a Reference List before the claims, or in the text itself; and, each of these documents or references ("herein-cited references"), as well as each document or reference cited in each of the herein-cited references (including any manufacturer's specifications, instructions, etc.), is hereby expressly incorporated herein by reference.

STATEMENT OF RIGHTS TO INVENTIONS MADE UNDER FEDERALLY SPONSORED RESEARCH

Research supporting this application was carried out by the United States of America as represented by the Secretary, Department of Health and Human Services. This research was supported by grant NCI K08118416 from the National Institute of Health. The Government may have certain rights in this invention.

BACKGROUND OF THE INVENTION

RNA interference refers to the process of sequence-specific post-transcriptional gene silencing in animals that is mediated by small inhibitory nucleic acid molecules (siRNAs) a double-stranded RNA (dsRNA) that is homologous in sequence to a portion of a targeted messenger RNA. See Fire, et al., Nature 391:806, 1998, and Hamilton, et al., Science 286:950-951, 1999. These dsRNAs serve as guide sequences for the multi-component nuclease machinery within the cell that degrade the endogenous-cognate mRNAs (i.e., mRNAs that share sequence identity with the introduced dsRNA).

The process of post-transcriptional gene silencing is thought to be an evolutionarily-conserved cellular defense mechanism used to prevent the expression of foreign genes and is commonly shared by diverse flora and fauna. Fire, et al., Trends Genet. 15:358, 1999. Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA.

RNAi has been studied in a variety of systems. Fire et al. were the first to observe RNAi in *C. elegans*. Nature 391:806, 1998. Bahramian & Zarbl and Wianny & Goetz describe RNAi mediated by dsRNA in mammalian systems. Molecular and Cellular Biology 19:274-283, 1999, and Nature Cell Biol. 2:70, 1999, respectively. Hammond, et al., describes RNAi in *Drosophila* cells transfected with dsRNA. Nature 404:293, 2000. Elbashir, et al., describe RNAi induced by introduction of duplexes of synthetic 21-nucleotide RNAs in cultured mammalian cells including human embryonic kidney and HeLa cells. Nature 411:494, 2001.

To date, siRNA is an emerging novel field with significant clinical implications. However, the technology is hampered by a number of limitations, such as difficulty and impracticality of its delivery in vivo. Although viral vector-based siRNA delivery systems have been widely used, their specificity and safety remains significant issue. While delivery of nucleic acids offers advantages over delivery of cytotoxic proteins such as reduced toxicity prior to internalization, there is a need for high specificity of delivery, which is currently unavailable with the present systems.

In view of some of the problems associated with gene therapy, there is a need for improved treatments which are more effective and are not associated with such disadvantages.

SUMMARY OF THE INVENTION

The inventors of the instant application have developed novel compositions and methods for delivering inhibitory oligonucleotides to cells in a targeted and efficient manner. The compositions and methods are based on utilizing a cell surface receptor targeting ligand, for example a chemokine, and a domain that binds an inhibitory oligonucleotide, to efficiently deliver the inhibitory oligonucleotide to the cell that expresses the cell surface receptor targeting ligand. Accordingly, the invention features compositions and methods that make use of complexes comprising one or more inhibitory nucleic acids and a targeting polypeptide, wherein the targeting polypeptide consists of a cell surface receptor ligand. The compositions can be used in methods of silencing gene expression in a cell, in delivering agents to a target cell, and in treating or preventing a disease or disorder in a subject.

In a first aspect, the invention features a complex comprising one or more inhibitory nucleic acids and a targeting polypeptide, wherein the targeting polypeptide comprises a cell surface receptor ligand.

In one embodiment, the targeting polypeptide further comprises a nucleic acid binding moiety. In a further embodiment, the nucleic acid binding moiety comprises a nucleic acid binding domain.

In another embodiment, the nucleic acid binding domain comprises protamine, or a fragment thereof. In a related embodiment, the protamine is human protamine.

In another further embodiment, the nucleic acid binding moiety comprises a viral antigen. In a related embodiment, the viral antigen is a viral capsid antigen. In a further related embodiment, the viral capsid antigen is selected from the group consisting of: gp120, gp160 and gp41.

In another embodiment, the inhibitory nucleic acid is a single stranded DNA or RNA. In a further related embodiment, the inhibitory nucleic acid is a double stranded DNA or RNA. In still another related embodiment, the nucleic acid binding moiety and the targeting polypeptide are separated by a spacer peptide. In one particular embodiment, the spacer peptide comprises SEQ ID NO: 5 (SDGGGSGGGGSLE). In another particular embodiment, the spacer peptide comprises SEQ ID NO: 6: (DGGGSGGGGSL).

In another embodiment, the double stranded RNA comprises one strand that is complementary to an RNA interference target, and another strand that is identical to an RNA interference target.

In a further embodiment, the inhibitory nucleic acid is selected from the group consisting of: short interfering nucleic acid (siNA), short interfering RNA (siRNA), double-stranded RNA (dsRNA), micro-RNA (miRNA), and short hairpin RNA (shRNA).

In another further embodiment, the cell surface receptor ligand is selected from the group consisting of: a cytokine, a chemokine, an antibody and a growth factor.

In one embodiment, the inhibitory nucleic acids comprise at least two double stranded RNAs.

In another embodiment, the inhibitory nucleic acids further comprise an agent. In a related embodiment, the agent is a label. In another related embodiment, the label is selected from a radiolabel or a fluorescent label. In still another embodiment, the agent is a therapeutic agent.

In another aspect, the invention features a complex comprising one or more inhibitory nucleic acids and a targeting polypeptide, wherein the targeting polypeptide further comprises a nucleic acid binding moiety, encoded by the nucleic acid set forth as SEQ ID NO: 1 or SEQ ID NO: 3.

In still another aspect, the invention features a complex comprising a targeting polypeptide and a nucleic acid binding moiety, encoded by a polypeptide comprising the amino acid sequence of SEQ ID NO: 2 or SEQ ID NO: 4.

In one embodiment of the above aspects, the complex further comprises an inhibitory nucleic acid.

In a related embodiment of the aspects described above, the one or more inhibitory nucleic acids and the targeting polypeptide are joined by a linker.

In another aspect, the invention features a fusion molecule comprising one or more inhibitory nucleic acids and a targeting polypeptide, wherein the targeting polypeptide comprises a cell surface receptor ligand.

In one embodiment, the targeting polypeptide further comprises a linker. In a related embodiment, the linker comprises a nucleic acid binding domain. In a further related embodiment, the nucleic acid binding domain comprises protamine, or a fragment thereof. In still another embodiment, the protamine is human protamine.

In another embodiment, the linker comprises a viral antigen. In a further embodiment, the viral antigen is a viral capsid antigen. In another related embodiment, the viral capsid antigen is selected from the group consisting of: gp120, gp160 and gp41.

In another embodiment, the inhibitory nucleic acid is a single stranded DNA or RNA. In a further related embodiment, the inhibitory nucleic acid is a double stranded DNA or RNA. In still another related embodiment, the nucleic acid binding moiety and the targeting polypeptide are separated by a spacer peptide. In one particular embodiment, the spacer peptide comprises SEQ ID NO: 5 (SDGGGSGGGGSLE). In another particular embodiment, the spacer peptide comprises SEQ ID NO: 6: (DGGGSGGGGSL). In another further embodiment, the spacer peptide comprises SEQ ID NO: 7 (GGGSGGGG). In another embodiment, the spacer peptide comprises SEQ ID NO: 8 (GGGGSGGGG).

In another embodiment, the double stranded RNA comprises one strand that is complementary to an RNA interference target, and another strand that is identical to an RNA interference target.

In a further embodiment, the inhibitory nucleic acid is selected from the group consisting of: short interfering nucleic acid (siNA), short interfering RNA (siRNA), double-stranded RNA (dsRNA), micro-RNA (miRNA), and short hairpin RNA (shRNA).

In another further embodiment, the cell surface receptor ligand is selected from the group consisting of: a cytokine, a chemokine, an antibody and a growth factor.

In preferred embodiments, the chemokine is selected from TARC/CCL17, MCP-1/CCL2 and RANTES/CCL5.

In one embodiment, the inhibitory nucleic acids comprise at least two double stranded RNAs.

In another embodiment, the inhibitory nucleic acids further comprise an agent. In a related embodiment, the agent is a label. In another related embodiment, the label is selected from a radiolabel or a fluorescent label. In still another embodiment, the agent is a therapeutic agent.

In another aspect, the invention features a fusion molecule comprising one or more inhibitory nucleic acids and a targeting polypeptide, wherein the targeting polypeptide further comprises a nucleic acid binding moiety, encoded by the nucleic acid set forth as SEQ ID NO: 1 or SEQ ID NO: 3.

In another aspect, the invention features a fusion molecule comprising a targeting polypeptide and a nucleic acid binding moiety, encoded by a polypeptide comprising the amino acid sequence of SEQ ID NO: 2 or SEQ ID NO: 4.

In one embodiment, the fusion molecule further comprises an inhibitory nucleic acid.

In another embodiment, the invention features a vector comprising the fusion molecule as described herein. The vector can be an adenoviral, lentiviral, or any type of viral vector. In other certain preferred embodiments on the invention, the vector comprises a promoter suitable for expression in a mammalian cell.

In other embodiments, the invention features a cell comprising the vector as described herein.

In still another aspect, the invention features a method of decreasing the level of gene expression in a cell comprising: contacting the cell with a complex comprising one or more inhibitory nucleic acids that decrease the expression of one or more target genes and a targeting polypeptide, wherein the targeting polypeptide comprises a cell surface receptor ligand, thereby decreasing the level of gene expression in the cell.

In another aspect, the invention features a method of delivering inhibitory RNA molecules into a cell, the method comprising contacting the cell with a complex comprising one or more double stranded RNAs and a targeting polypeptide, wherein the targeting polypeptide comprises a cell surface receptor ligand, thereby delivering inhibitory RNA molecules into a cell.

In still another aspect, the invention features a method of treating or preventing a disease or disorder in a subject by decreasing the level of gene expression comprising: contacting the cell with a complex comprising one or more inhibitory nucleic acids that reduce the expression of one or more target genes and a targeting polypeptide, wherein the targeting polypeptide comprises a cell surface receptor ligand, thereby treating or preventing a disease or disorder in a subject.

In one embodiment, the method further comprises treatment with an additional agent. In a related embodiment, the agent is a therapeutic agent.

In still another aspect, the invention features a method of delivering one or more agents to a target cell comprising: contacting the cell with a complex comprising one or more inhibitory nucleic acids that reduce the expression of one or more target genes, wherein the one or more inhibitory nucleic acids are coupled to an agent, and a targeting polypeptide, wherein the targeting polypeptide comprises of a cell surface receptor ligand, thereby delivering the agent to a target cell.

In one embodiment, the agent is a therapeutic agent.

In another embodiment, the agent is a label.

In another aspect, the invention features a method of delivering an imaging agent into a cell in a subject comprising: contacting the cell with a complex comprising one or more inhibitory nucleic acids that reduce the expression of one or more target genes, wherein the one or more inhibitory nucleic acids are coupled to the imaging agent, and a targeting polypeptide, wherein the targeting polypeptide consists of a cell surface receptor ligand, delivering the agent into the cell.

In one embodiment, the method is used to determine prognosis.

In another embodiment, the method is used to determine course of treatment.

In one embodiment of any one of the above aspects, the targeting polypeptide further comprises a nucleic acid binding moiety. In a related embodiment, the nucleic acid binding moiety comprises a nucleic acid binding domain.

In a further related embodiment, the nucleic acid binding domain comprises protamine, or a fragment thereof. In still another embodiment, the protamine is human protamine.

In another embodiment, the linker comprises a viral antigen. In a further embodiment, the viral antigen is a viral capsid antigen. In another related embodiment, the viral capsid antigen is selected from the group consisting of: gp120, gp160 and gp41.

In another embodiment, the inhibitory nucleic acid is a single stranded DNA or RNA. In a further related embodiment, the inhibitory nucleic acid is a double stranded DNA or RNA. In still another related embodiment, the nucleic acid binding moiety and the targeting polypeptide are separated by a spacer peptide. In one particular embodiment, the spacer peptide comprises SEQ ID NO: 5 (SDGGGSGGGGSLE). In another particular embodiment, the spacer peptide comprises SEQ ID NO: 6: (DGGGSGGGGSL). In another embodiment, the spacer peptide comprises SEQ ID NO: 7 (GGGSGGGG). In still another embodiment, the spacer peptide comprises SEQ ID NO: 8 (GGGGSGGGG).

In another embodiment, the double stranded RNA comprises one strand that is complementary to an RNA interference target, and another strand that is identical to an RNA interference target.

In a further embodiment, the inhibitory nucleic acid is selected from the group consisting of: short interfering nucleic acid (siNA), short interfering RNA (siRNA), double-stranded RNA (dsRNA), micro-RNA (miRNA), and short hairpin RNA (shRNA).

In another further embodiment, the cell surface receptor ligand is selected from the group consisting of: a cytokine, a chemokine, an antibody and a growth factor.

In preferred embodiments, the chemokine is selected from TARC/CCL17, MCP-1/CCL2 and RANTES/CCL5.

In one embodiment, the inhibitory nucleic acids comprise at least two double stranded RNAs.

In another embodiment, the inhibitory nucleic acids further comprise an agent. In a related embodiment, the agent is a label. In another related embodiment, the label is selected from a radiolabel or a fluorescent label. In still another embodiment, the agent is a therapeutic agent.

In one embodiment of any one of the above aspects, the targeting polypeptide and the nucleic acid binding moiety are encoded by a nucleic acid sequence selected from the group consisting of: SEQ ID NO: 1 and SEQ ID NO: 3.

In another embodiment of any one of the above aspects, the cell is a cultured cell.

In another embodiment of any one of the above aspects, the cell is part of a subject animal.

In another embodiment of any one of the above aspects, the cell is selected from the group consisting of: immune cells, epithelial cells, endothelial cells, cardiac cells, neural cells, hepatocytes, lymphocytes and myocytes.

In another embodiment of any one of the above aspects, the cell is a malignant cell. In still another embodiment of any one of the above aspects, the cell is a stem cell.

In another embodiment of any one of the above aspects, the subject is a mammal. In still another embodiment of any one of the above aspects, the subject is a human. In yet another embodiment of any one of the above aspects, the subject is suffering from a neoplasia. In another further embodiment of any one of the above aspects, the subject is suffering from an immunological disease or disorder.

In certain embodiments, the neoplasia may be leukemia. In other embodiments, the neoplasia may be breast cancer.

In another embodiment of any one of the above aspects, the method is used to diagnose a metastasis.

In another aspect, the invention features a pharmaceutical composition for treating or preventing a disease or disorder in a subject comprising one or more inhibitory nucleic acids and a targeting polypeptide, wherein the targeting polypeptide comprises a cell surface receptor ligand, thereby treating or preventing a disease or disorder in a subject.

In one embodiment, the targeting polypeptide and a nucleic acid binding moiety are encoded by a nucleic acid sequence selected from the group consisting of: SEQ ID NO: 1 and SEQ ID NO: 3.

In another embodiment, the pharmaceutical composition further comprises an additional agent.

In another aspect, the invention features a pharmaceutical composition for delivering one or more agents to a target cell comprising one or more inhibitory nucleic acids, wherein the one or more inhibitory nucleic acids are coupled to an agent, and a targeting polypeptide, wherein the targeting polypeptide consists of a cell surface receptor ligand, thereby treating or preventing a disease or disorder in a subject.

In one embodiment, the agent is a therapeutic agent.

In another aspect, the invention features a kit comprising the complex of any one of the aspects as described herein, and instructions for use.

In another aspect, the invention features a kit comprising the fusion molecule of any one of the aspects as described herein, and instructions for use.

Other features and advantages of the invention will be apparent from the detailed description, and from the claims.

BRIEF DESCRIPTION OF THE DRAWINGS

FIG. 2 shows SEQ ID NO: 1 and SEQ ID NO: 2. The sequence represented by SEQ ID NO: 1 (top) is the DNA sequence of the complex of the invention that contains TARC associated with protamine fragment. The sequence represented by SEQ ID NO: 2 is the protein sequence of the complex that contains TARC associated with protamine fragment. The sequence represented by SEQ ID NO: 2 (bottom) is the mature sequence of human TARC/CCL17 that contains Met (Italic, underlined) and protamine fragment (Italic). The spacer peptide fragment (underlined small letters) is used to separate chemokine from protamine. The construct also contains c-myc-tag and six His residues for analytical use and protein purification purposes. The c-myc-tag and six His residues are not necessary, and some constructs do not have them.

FIG. 3 shows SEQ ID NO: 3 and SEQ ID NO: 4. The sequence represented by SEQ ID NO: 3 (top) is the DNA sequence of the complex that contains TARC associated with RNA binding domain of HBcAg. The sequence represented by SEQ ID NO: 4 is the protein sequence of the complex that contains TARC associated with the RNA binding domain of HBcAg. The sequence represented by SEQ ID NO: 4 (bottom) is the mature sequence of human TARC/CCL17 that contains Met (Italic, underlined) and RNA binding domain of HBcAg (Italic). The spacer peptide fragment (underlined small letters) is used to separate chemokine from RNA binding domain of HBcAg. The construct also contains five His residues for analytical use and protein purification purposes. The five His residues are not necessary, and some constructs do not have them.

FIG. 4 shows SEQ ID NO: 5, SEQ ID NO: 6, SEQ ID NO: 7 and SEQ ID NO: 8. The sequence represented by SEQ ID NOs 5-8 corresponds to exemplary spacer sequences that separate the nucleic acid binding moiety and the targeting polypeptide.

FIG. 5 shoes SEQ ID NO: 9, SEQ IS NO: 10 and SEQ ID NO: 11. The sequence represented by SEQ ID NO: 9 is the protein sequence of the complex corresponding to TARC-Arp, human TARC/CCL17 fused with a hypothetical RNA-binding domain of HBV virus (underlined). In SEQ ID NO: 9, a spacer sequence was inserted between TARC/CCL17 and the hypothetical RNA-binding domain of HBV virus (Italic). SEQ ID NO: 10 is the protein sequence of the complex corresponding to RANTES-Arp, human RANTES/CCL5 fused with a hypothetical RNA-binding domain of HBV virus (underlined). In SEQ ID NO: 10, a spacer sequence was inserted between RANTES and the hypothetical RNA-binding domain of HBV virus (Italic). SEQ ID NO: 11 is the protein sequence of the complex corresponding to MCP1-Arp, human MCP1/CCL2 fused with a hypothetical RNA-binding domain of HBV virus (underlined). In SEQ ID NO: 11, a spacer sequence was inserted between MCP-1 and the hypothetical RNA-binding domain of HBV virus (Italic).

DETAILED DESCRIPTION

Figure 1A:
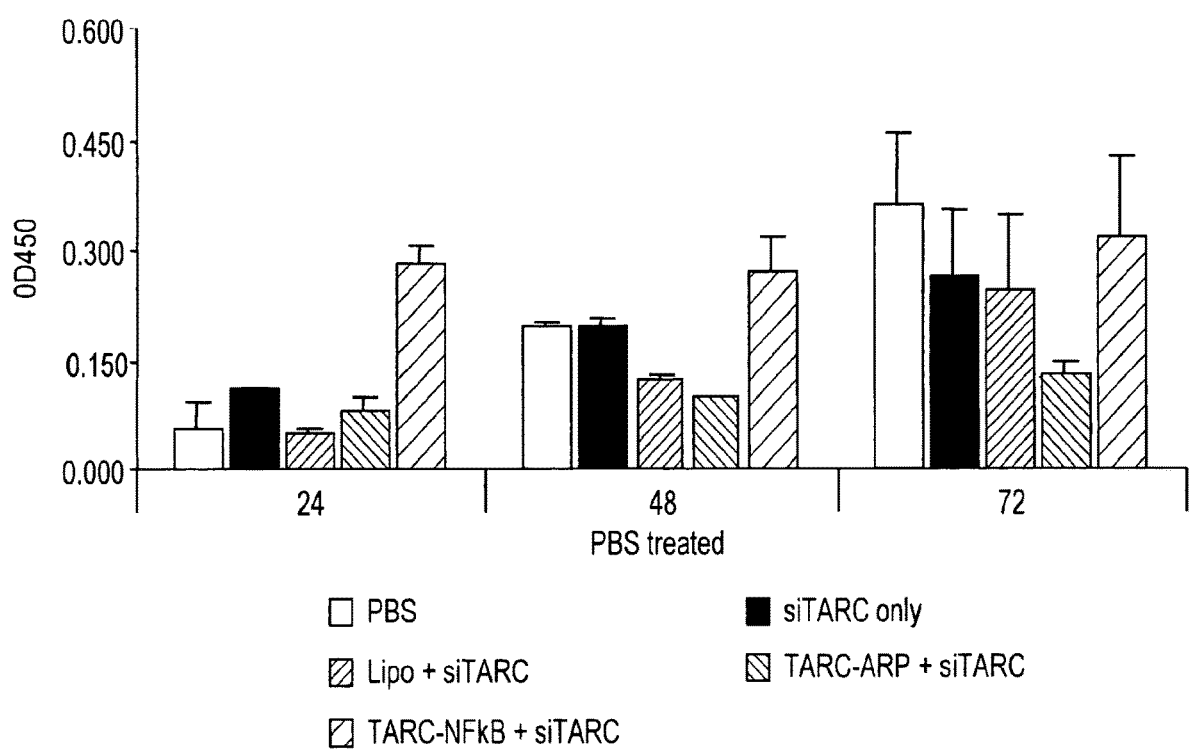
FIG. 1 (A-C) are graphs that show the complex of the invention that targets chemokine CCR4 (TARC-ARP) (thymus- and activation-regulated chemokine/TARC) and can deliver siRNA against chemokine TARC/CCL17 (siTARC) and efficiently abrogate production/secretion of TARC/CCL17 from breast cancer 4T1 cells. Panel 1A is a graph that shows the detection of mTARC in the supernatant from 4T1.WT cells without LPS treatment. Panel 1B is a graph that shows the detection of mTARC in the supernatant from 4T1.WT cells with 100 ng/ml LPS treatment. Panel 1C shows results from immunflourescence experiments demonstrating that the TARC-ARP complex can effectively deliver siRNA to breast cancer cells that express CCR4.

The instant invention describes novel compositions and methods for delivering inhibitory oligonucleotides, for example siRNA, to cells utilizing the ligands to cell surface receptors. The compositions of the invention can efficiently deliver inhibitory oligonucleotides to target cells that express the cell surface receptors effectively and in a directed manner. In preferred aspects of the invention, the composition comprises a recombinant protein that consists of two main portions: the cell surface receptor-targeting ligand, for example a chemokine that is associated with a domain that binds the inhibitory oligonucleotide. Thus, the composition can encompass any cell surface receptor from any species, for example human, mouse, rat, and viral cell surface targets. The inhibitory nucleotide binding domain can be any peptide that can bind RNA, including the poly arginine region of protamine and the RNA binding peptides from viral antigens.

Definitions

The following definitions are provided for specific terms which are used in the following written description.

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

As used in the specification and claims, the singular form "a", "an" and "the" include plural references unless the context clearly dictates otherwise.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments. The terms "administration" or "administering" are defined to include an act of providing a compound or pharmaceutical composition of the invention to a subject in need of treatment.

The phrase "in combination with" is intended to refer to all forms of administration that provide the inhibitory nucleic acid molecule and the chemotherapeutic agent together, and can include sequential administration, in any order.

By "subject" is intended to include vertebrates, preferably a mammal. Mammals include, but are not limited to, humans.

By "cell surface receptor specific ligand" as used herein is meant to refer to a molecule that binds to a cell surface receptor or cell surface antigen. In preferred examples, a ligand is then coupled to an inhibitory nucleotide.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids. In preferred examples, the fragment is a fragment of SEQ ID NO: 1 or SEQ ID NO: 3.

By "inhibitory nucleic acid" is meant a single or double-stranded RNA, siRNA (short interfering RNA), shRNA (short hairpin RNA), or antisense RNA, or a portion thereof, or a mimetic thereof, that when administered to a mammalian cell results in a decrease (e.g., by 10%, 25%, 50%, 75%, or even 90-100%) in the expression of a target gene. Typically, a nucleic acid inhibitor comprises or corresponds to at least a portion of a target nucleic acid molecule, or an ortholog thereof, or comprises at least a portion of the complementary strand of a target nucleic acid molecule.

Nucleic acid molecules useful in the methods of the invention include a nucleic acid molecule encoding SEQ ID NO: 1 or SEQ ID NO: 3 or fragments thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

The term "antisense nucleic acid", as used herein, refers to a non-enzymatic nucleic acid molecule that binds to target RNA by means of RNA-RNA or RNA-DNA or RNA-PNA (protein nucleic acid; Egholm et al., 1993 Nature 365, 566) interactions and alters the activity of the target RNA (for a review, see Stein and Cheng, 1993 Science 261, 1004 and Woolf et al., U.S. Pat. No. 5,849,902). Typically, antisense molecules are complementary to a target sequence along a single contiguous sequence of the antisense molecule. However, in certain embodiments, an antisense molecule can bind to substrate such that the substrate molecule forms a loop, and/or an antisense molecule can bind such that the antisense molecule forms a loop. Thus, the antisense molecule can be complementary to two (or even more) non-contiguous substrate sequences or two (or even more) non-contiguous sequence portions of an antisense molecule can be complementary to a target sequence or both. For a review of antisense strategies, see Schmajuk et al., 1999, J. Biol. Chem., 274, 21783-21789, Delihas et al., 1997, Nature, 15, 751-753, Stein et al., 1997, Antisense N. A. Drug Dev., 7, 151, Crooke, 2000, Methods Enzymol., 313, 3-45; Crooke, 1998, Biotech. Genet. Eng. Rev., 15, 121-157, Crooke, 1997, Ad. Pharmacol., 40, 1-49. In addition, antisense DNA can be used to target RNA by means of DNA-RNA interactions, thereby activating RNase H, which digests the target RNA in the duplex. The antisense oligonucleotides can comprise one or more RNAse H activating region, which is capable of activating RNAse H cleavage of a target RNA. Antisense DNA can be synthesized chemically or expressed via the use of a single stranded DNA expression vector or equivalent thereof.

By "thymus- and activation-regulated chemokine (TARC)" is meant to refer to a Th2-type CC chemokine that is one of the high-affinity ligands for CCR4, a chemokine receptor.

By "small molecule" inhibitor is meant a molecule of less than about 3,000 daltons having antagonist activity against a specified target.

By "RNA" is meant to include polynucleotide molecules comprising at least one ribonucleotide residue. The term "ribonucleotide" is meant to include nucleotides with a hydroxyl group at the 2' position of a .beta.-D-ribo-furanose moiety. The term RNA includes, for example, double-stranded RNAs; single-stranded RNAs; and isolated RNAs such as partially purified RNA, essentially pure RNA, synthetic RNA, recombinantly produced RNA, as well as altered RNA that differ from naturally occurring RNA by the addition, deletion, substitution and/or alteration of one or more nucleotides. Such alterations can include addition of non-nucleotide material, such as to the end(s) of the siRNA or internally, for example at one or more nucleotides of the RNA. As disclosed in detail herein, nucleotides in the siRNA molecules of the instant invention can also comprise non-standard nucleotides, such as non-naturally occurring nucleotides or chemically synthesized nucleotides or deoxy-nucleotides. These altered RNAs can be referred to as analogs or analogs of naturally-occurring RNA.

The term "siRNA" refers to small interfering RNA; a siRNA is a double stranded RNA that "corresponds" to or matches a reference or target gene sequence. This matching need not be perfect so long as each strand of the siRNA is capable of binding to at least a portion of the target sequence. SiRNA can be used to inhibit gene expression, see for example Bass, 2001, Nature, 411, 428 429; Elbashir et al., 2001, Nature, 411, 494 498; and Zamore et al., Cell 101:25-33 (2000).

By "nucleic acid binding domain" (NABD) is meant to refer to a molecule, for example a protein, polypeptide, or peptide, that binds nucleic acids, such as DNA or RNA. The NABD may bind to single or double strands of RNA or DNA or mixed RNA/DNA hybrids. The nucleic acid binding domain may bind to a specific sequence or bind irrespective of the sequence.

By "nucleic acid" is meant an oligomer or polymer of ribonucleic acid or deoxyribonucleic acid, or analog thereof. This term includes oligomers consisting of naturally occurring bases, sugars, and intersugar (backbone) linkages as well as oligomers having non-naturally occurring portions which function similarly. In preferred embodiments, "nucleic acids" refer to RNA or DNA that are intended for internalization into a cell.

The term "pharmaceutically-acceptable excipient" as used herein means one or more compatible solid or liquid filler, diluents or encapsulating substances that are suitable for administration into a human.

Compositions

As described herein the present invention features compositions and methods that make use of complexes comprising one or more inhibitory nucleic acids and a targeting polypeptide, wherein the targeting polypeptide comprises of a cell surface receptor ligand. The compositions can be used in methods of silencing, or knocking down, gene expression in a cell, in delivering agents to a target cell, and in treating or preventing a disease or disorder in a subject.

In one aspect, the complex comprises one or more inhibitory nucleic acids and a targeting polypeptide, wherein the targeting polypeptide comprises of a cell surface receptor ligand. In certain examples, the targeting polypeptide further comprises a nucleic acid binding moiety.

A cell surface receptor specific ligand as used herein is defined as any molecule that binds to a cellular receptor or cell surface antigen. A ligand is then coupled to an appropriate inhibitory nucleic acid, e.g. a dsRNA binding protein. The ligand is a natural- or engineered-peptide or protein, such as is commercially available (Antibodies by Design, MorphoSys, Martinsried, Germany) (U.S. Pat. Nos. 5,514, 548; 6,653,068 B2; 6,667,150 B1; 6,696,245; 6,753,136 B1; U.S. 2004/017291 A1).

In preferred embodiments, the cell surface receptor ligand is selected from the group consisting of a cytokine, a chemokine, an antibody, a growth factor.

Cytokines are small secreted proteins which mediate and regulate immunity, inflammation, and hematopoiesis. Cytokines are produced de novo in response to an immune stimulus. Cytokine is a general name; other names include lymphokine (cytokines made by lymphocytes), monokine (cytokines made by monocytes), chemokine (cytokines with chemotactic activities), and interleukin (cytokines made by one leukocyte and acting on other leukocytes). Cytokines may act on the cells that secrete them (autocrine action), on nearby cells (paracrine action), or in some instances on distant cells (endocrine action). Cytokines act on their target cells by binding specific membrane receptors. The receptors and their corresponding cytokines have been divided into several families based on their structure and activities. Hematopoietin family receptors are dimers or trimers with conserved cysteines in their extracellular domains and a conserved Trp-Ser-X-Trp-Ser sequence. Examples are receptors for IL-2 through IL-7 and GM-CSF. Interferon family receptors have the conserved cysteine residues but not the Trp-Ser-X-Trp-Ser sequence, and include the receptors for IFNa, IFNb, and IFNg. Tumor Necrosis Factor family receptors have four extracellular domains; they include receptors for soluble TNFa and TNFb as well as membrane-bound CD40 (important for B cell and macrophage activation) and Fas (which signals the cell to undergo apoptosis). Chemokine family receptors have seven transmembrane helices and interact with G protein. This family includes receptors for IL-8, MIP-1 and RANTES. Chemokine receptors CCR5 and CXCR4 are used by HIV to preferentially enter either macrophages or T cells.

Chemokines are a family of small cytokines that are secreted by cells. Chemokine receptors are G protein-coupled receptors containing 7 transmembrane domains that are found on the surface of leukocytes. Approximately 19 different chemokine receptors have been characterized to date, which are divided into four families depending on the type of chemokine they bind; CXCR that bind CXC chemokines, CCR that bind CC chemokines, CX3CR1 that binds the sole CX3C chemokine (CX3CL1), and XCR1 that binds the two XC chemokines (XCL1 and XCL2). They share many structural features; they are similar in size (with about 350 amino acids), have a short, acidic N-terminal end, seven helical transmembrane domains with three intracellular and three extracellular hydrophilic loops, and an intracellular C-terminus containing serine and threonine residues important for receptor regulation. The first two extracellular loops of chemokine receptors each have a conserved cysteine residue that allows formation of a disulfide bridge between these loops. G proteins are coupled to the C-terminal end of the chemokine receptor to allow intracellular signaling after receptor activation, while the N-terminal domain of the chemokine receptor determines ligand binding specificity.

Thus, in certain exemplary embodiments, the invention features complexes comprising one or more inhibitory nucleic acids and a targeting polypeptide, wherein the targeting polypeptide comprises a cell surface receptor ligand. The rageting polypeptide can comprise a chemokine. There are more than 50 chemokines known, and any may be suitable for use in the invention as claimed.

In certain examples, exemplary chemokines are selected from, but not necessarily limited to TARC/CCL17, MCP-1/CCL-2 and RANTES/CCL5.

There are about 18 chemokine receptors known. Therefore, the present invention allows for complexes that target each of the 18 chemokine receptors.

If the engineered ligand is an immunoglobulin, the carboxy terminus of the molecule is at the variable end of the protein, and the amino terminus is available for covalently binding to the RNA binding protein to which the dsRNA is adsorbed. Because of the relatively large size of immunoglobulin molecules, preferably a Fab fragment is used as the ligand rather than the entire immunoglobin. More preferably, a $(Fab')_2$ fragment is provided that allows for divalent binding as would occur with the entire immunoglobin without the encumbrance of the Fc component. Bridging of cell surface receptors by a divalent $(Fab')_2$ fragment facilitates activation of the signaling pathway and subsequent internalization of the receptor-ligand combination in some internalization processes.

As described above, in certain examples, the targeting polypeptide further comprises a nucleic acid binding moiety. The nucleic acid binding moiety is used to associate the targeting polypeptide and the inhibitory nucleic acid.

In certain examples, the nucleic acid binding domain comprises protamine, or a fragment thereof. Protamines are small, arginine-rich, nuclear proteins.

In other certain examples, the nucleic acid binding domain comprises a viral antigen. The viral antigen can be, in certain examples, a viral capsid antigen. Any viral capsid antigen is suitable for use in the invention, as long as it binds the inhibitory nucleic acid; however in certain examples, the viral capsid acid is selected from, but not limited to, gp120, gp160, gp41. In certain examples, the one or more inhibitory nucleic acids and the targeting polypeptide are joined by a linker.

The invention can also feature fusion molecules. A fusion molecule may comprise one or more inhibitory nucleic acids and a targeting polypeptide, wherein the targeting polypeptide comprises a cell surface receptor ligand. In certain examples, the targeting polypeptide can further comprise a linker.

Exemplary fusion molecules of the invention may comprise one or more inhibitory nucleic acids and a targeting polypeptide, wherein the targeting polypeptide further comprises a nucleic acid binding moiety, encoded by the nucleic acid sequence set forth as SEQ ID NO: 1 or SEQ ID NO: 3.

Exemplary fusion molecules of the invention may comprise a targeting polypeptide and a nucleic acid binding moiety, encoded by a polypeptide comprising the amino acid sequence of SEQ ID NO: 2, SEQ ID NO: 4, SEQ ID NO: 9, SEQ ID NO: 10 or SEQ ID NO: 11.

The linker may comprise a nucleic acid binding domain. As described, the nucleic acid binding domain can comprise protamine, or a fragment thereof. In certain cases, the protamine is human protamine. In other certain cases, the linker comprises a viral antigen, which, for example may be, but is not limited to, a viral antigen, for example a viral capsid antigen (e.g. gp120, gp160 or gp41).

Any linker can be used that connects or links the targeting polypeptide and the inhibitory nucleic acid. In certain examples, the targeting polypeptide can be linked to the inhibitory nucleic acid by simply a covalent bond that covalently bonds a hydrophilic polymer to a residue derived from the inhibitory nucleic acid.

The term “covalent attachment” means that the polypeptide and the non-polypeptide moiety, e.g. the nucleic acid moiety, are either directly covalently joined to one another, or else are indirectly covalently joined to one another through an intervening moiety or moieties, such as a linker, or a bridge, or a spacer, moiety or moieties. Preferably, a conjugated polypeptide is soluble at relevant concentrations and conditions, i.e. soluble in physiological fluids. There is no limit to the linker mediating the covalent bond between the hydrophilic polymer and the end group of the residue derived from the inhibitory nucleic acid. In certain cases, it is preferable that the linker be degradable on necessity under predetermined conditions. In other certain cases, the linker can be a polyalkylene glycol. For example, the linking moiety is polyethylene glycol (PEG). In other certain cases, the linker is a disulfide bond.

In one embodiment, the targeting polypeptide and the inhibitory polynucleotide are linked by the PEG linking moiety, such that the primary structure of the nucleic acid composition is a linear arrangement in which the targeting polypeptide is linked to a first terminus of the PEG linking moiety and the nucleic acid is linked to a second terminus of the PEG linking moiety.

US Application 20070231392, incorporated by reference in its entirety herein, describes a non-viral carrier for nucleic acid delivery in vitro and in vivo. The polycation polymers described may form complexes with biomolecules and thus are useful as carriers for the delivery of biomolecules to cells. Examples of biomolecules that form complexes with the compound of the Formula I include nucleic acids, proteins, peptides, lipids, and carbohydrates. Examples of nucleic acids include DNA, single strand RNA, double strand RNA, ribozyme, DNA-RNA hybridizer, and antisense DNA, e.g., antisense oligo. Preferred nucleic acids are siRNA.

The functional RNA interference activity of RNAi transported into target cells while adsorbed to a complex as described herein containing protamine as the RNA bonding protein and a Fab fragment specific for the HIV envelope protein gp160 has been previously demonstrated (Song et al. 2005). Similarly, functional RNA interference activity of interfering RNA transported into target cells as a cargo molecule attached to HIV-1 transactivator of transcription (TAT) peptide47-57 has been demonstrated (Chiu Y-L et al. 2004). The functional RNA interference activity of interfering RNA transported into target cells as a cargo molecule attached to pentratin has also been demonstrated (Muratovska and Eccles 2004).

In certain embodiments, the inhibitory nucleotides are delivered into the cell by internalization of the receptor.

In the event a targeted cell receptor is a unique receptor that is not naturally internalized, that receptor is nonetheless suitable as a target by incorporating an internalization moiety such as an arginine-rich membrane permeable peptide within the ligand or attaching to the ligand such as an arginine-rich membrane permeable peptide, pentratin, or transportan as detailed in U.S. Pat. No. 6,692,935 B1 or U.S. Pat. No. 6,294,353 B1.

Inhibitory Nucleic Acids

As described herein, the invention describes complexes comprising one or more inhibitory nucleic acids and a targeting polypeptide, wherein the targeting polypeptide consists of a cell surface receptor ligand.

The complex comprises inhibitory nucleic acids that can be small nucleic acid molecules, such as short interfering nucleic acid (siNA), short interfering RNA (siRNA), double-stranded RNA (dsRNA), micro-RNA (miRNA), and short hairpin RNA (shRNA) molecules capable of mediating RNA interference (RNAi) against target gene expression. Such small nucleic acid molecules are useful, in certain examples, in providing compositions for treatment of traits, diseases and conditions that can respond to modulation of gene expression in a subject or organism.

RNA interference refers to the process of sequence-specific post-transcriptional gene silencing in animals mediated by short interfering RNAs (siRNAs) (Zamore et al., 2000, Cell, 101, 25-33; Fire et al., 1998, Nature, 391, 806; Hamilton et al., 1999, Science, 286, 950-951; Lin et al., 1999, Nature, 402, 128-129; Sharp, 1999, Genes & Dev., 13:139-141; and Strauss, 1999, Science, 286, 886). The corresponding process in plants (Heifetz et al., International PCT Publication No. WO 99/61631) is commonly referred to as post-transcriptional gene silencing or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla (Fire et al., 1999, Trends Genet., 15, 358). Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA. The presence of dsRNA in cells triggers the RNAi response through a mechanism that has yet to be fully characterized. This mechanism appears to be different from other known mechanisms involving double stranded RNA-specific ribonucleases, such as the interferon response that results from dsRNA-mediated activation of protein kinase PKR and 2',5'-oligoadenylate synthetase resulting in non-specific cleavage of mRNA by ribonuclease L (see for example U.S. Pat. Nos. 6,107,094; 5,898,031; Clemens et al., 1997, J. Interferon & Cytokine Res., 17, 503-524; Adah et al., 2001, Curr. Med. Chem., 8, 1189).

Haeberli et al. in US Application No. 20070042983, incorporated by reference in its entirety herein, describe compounds, compositions, and methods useful for modulating gene expression using short interfering nucleic acid (siNA) molecules.

For example, an inhibitory nucleotide of the invention may comprise modified nucleotides while maintaining the ability to mediate RNAi. The modified nucleotides can be used to improve in vitro or in vivo characteristics such as stability, activity, and/or bioavailability. For example, a siNA molecule of the invention can comprise modified nucleotides as a percentage of the total number of nucleotides present in the siNA molecule. As such, a siNA molecule of the invention can generally comprise about 5% to about 100% modified nucleotides (e.g., about 5%, 10%, 15%, 20%, 25%, 30%, 35%, 40%, 45%, 50%, 55%, 60%, 65%, 70%, 75%, 80%, 85%, 90%, 95% or 100% modified nucleotides). The actual percentage of modified nucleotides present in a given siNA molecule will depend on the total number of nucleotides present in the siNA. If the siNA molecule is single stranded, the percent modification can be based upon the total number of nucleotides present in the single stranded siNA molecules. Likewise, if the siNA molecule is double stranded, the percent modification can be based upon the total number of nucleotides present in the sense strand, antisense strand, or both the sense and antisense strands.

For example, an inhibitory nucleotide of the invention may comprise a double-stranded short interfering nucleic acid (siNA) molecule that down-regulates expression of a target gene or that directs cleavage of a target RNA. In one embodiment, the double stranded siNA molecule comprises one or more chemical modifications and each strand of the double-stranded siNA is about 21 nucleotides long. In one embodiment, the double-stranded siNA molecule does not contain any ribonucleotides. In another embodiment, the double-stranded siNA molecule comprises one or more ribonucleotides. In one embodiment, each strand of the double-stranded siNA molecule independently comprises about 15 to about 30 (e.g., about 15, 16, 17, 18, 19, 20, 21, 22, 23, 24, 25, 26, 27, 28, 29, or 30) nucleotides, wherein each strand comprises about 15 to about 30 (e.g., about 15, 16, 17, 18, 19, 20, 21, 22, 23, 24, 25, 26, 27, 28, 29, or 30) nucleotides that are complementary to the nucleotides of the other strand. In one embodiment, one of the strands of the double-stranded siNA molecule comprises a nucleotide sequence that is complementary to a nucleotide sequence or a portion thereof of the gene, and the second strand of the double-stranded siNA molecule comprises a nucleotide sequence substantially similar to the nucleotide sequence of the gene or a portion thereof.

For example, an inhibitory nucleotide of the invention may comprise a double-stranded short interfering nucleic acid (siNA) molecule that down-regulates expression of a target gene or that directs cleavage of a target RNA, comprising an antisense region, wherein the antisense region comprises a nucleotide sequence that is complementary to a nucleotide sequence of the gene or a portion thereof, and a sense region, wherein the sense region comprises a nucleotide sequence substantially similar to the nucleotide sequence of the gene or a portion thereof. In one embodiment, the antisense region and the sense region independently comprise about 15 to about 30 (e.g. about 15, 16, 17, 18, 19, 20, 21, 22, 23, 24, 25, 26, 27, 28, 29, or 30) nucleotides, wherein the antisense region comprises about 15 to about 30 (e.g. about 15, 16, 17, 18, 19, 20, 21, 22, 23, 24, 25, 26, 27, 28, 29, or 30) nucleotides that are complementary to nucleotides of the sense region.

For example, an inhibitory nucleotide of the invention may comprise a double-stranded short interfering nucleic acid (siNA) molecule that down-regulates expression of a target gene or that directs cleavage of a target RNA, comprising a sense region and an antisense region, wherein the antisense region comprises a nucleotide sequence that is complementary to a nucleotide sequence of RNA encoded by the gene or a portion thereof and the sense region comprises a nucleotide sequence that is complementary to the antisense region.

For example, an inhibitory nucleotide of the invention may comprise a double-stranded short interfering nucleic acid (siNA) molecule that down-regulates expression of a target gene or that directs cleavage of a target RNA, wherein the siNA molecule comprises about 15 to about 30 (e.g. about 15, 16, 17, 18, 19, 20, 21, 22, 23, 24, 25, 26, 27, 28, 29, or 30) base pairs, and wherein each strand of the siNA molecule comprises one or more chemical modifications. In another embodiment, one of the strands of the double-stranded siNA molecule comprises a nucleotide sequence that is complementary to a nucleotide sequence of a gene or a portion thereof, and the second strand of the double-stranded siNA molecule comprises a nucleotide sequence substantially similar to the nucleotide sequence or a portion thereof of the gene. In another embodiment, one of the strands of the double-stranded siNA molecule comprises a nucleotide sequence that is complementary to a nucleotide sequence of a gene or portion thereof, and the second strand of the double-stranded siNA molecule comprises a nucleotide sequence substantially similar to the nucleotide sequence or portion thereof of the gene. In another embodiment, each strand of the siNA molecule comprises about 15 to about 30 (e.g. about 15, 16, 17, 18, 19, 20, 21, 22, 23, 24, 25, 26, 27, 28, 29, or 30) nucleotides, and each strand comprises at least about 15 to about 30 (e.g. about 15, 16, 17, 18, 19, 20, 21, 22, 23, 24, 25, 26, 27, 28, 29, or 30) nucleotides that are complementary to the nucleotides of the other strand.

For example, an inhibitory nucleic acid of the invention may comprise a double-stranded short interfering nucleic acid (siNA) molecule that down-regulates expression of a target gene or that directs cleavage of a target RNA comprising a sense region and an antisense region, wherein the antisense region comprises a nucleotide sequence that is complementary to a nucleotide sequence of RNA encoded by the target gene or a portion thereof and the sense region comprises a nucleotide sequence that is complementary to the antisense region, and wherein the siNA molecule has one or more modified pyrimidine and/or purine nucleotides. In one embodiment, the pyrimidine nucleotides in the sense region are 2'-O-methylpyrimidine nucleotides or 2'-deoxy-2'-fluoro pyrimidine nucleotides and the purine nucleotides present in the sense region are 2'-deoxy purine nucleotides. In another embodiment, the pyrimidine nucleotides in the sense region are 2'-deoxy-2'-fluoro pyrimidine nucleotides and the purine nucleotides present in the sense region are 2'-O-methyl purine nucleotides. In another embodiment, the pyrimidine nucleotides in the sense region are 2'-deoxy-2'-fluoro pyrimidine nucleotides and the purine nucleotides present in the sense region are 2'-deoxy purine nucleotides. In one embodiment, the pyrimidine nucleotides in the antisense region are 2'-deoxy-2'-fluoro pyrimidine nucleotides and the purine nucleotides present in the antisense region are 2'-O-methyl or 2'-deoxy purine nucleotides. In another embodiment of any of the above-described siNA molecules, any nucleotides present in a non-complementary region of the sense strand (e.g. overhang region) are 2'-deoxy nucleotides.

For example, an inhibitory nucleic acid of the invention may comprise a double-stranded short interfering nucleic acid (siNA) molecule that down-regulates expression of a target gene or that directs cleavage of a target RNA, wherein the siNA molecule is assembled from two separate oligonucleotide fragments wherein one fragment comprises the sense region and the second fragment comprises the antisense region of the siNA molecule, and wherein the fragment comprising the sense region includes a terminal cap moiety at the 5'-end, the 3'-end, or both of the 5' and 3' ends of the fragment.

In certain examples, the inhibitory nucleic acid in the complex is a single stranded DNA or RNA, and may comprise two or more single stranded DNAs or RNAs. In other examples, the inhibitory nucleic acid is a double stranded DNA or RNA, and may comprise two or more double stranded DNAs or RNAs. Thus, the invention is suitable is certain examples for modulating the expression of more than one target gene in a subject or organism Exemplary complexes of the invention may comprise a targeting polypeptide and a nucleic acid binding moiety, wherein the targeting polypeptide and the nucleic acid binding domain are encoded by the nucleic acid sequence set forth as SEQ ID NO: 1 or SEQ ID NO: 3.

Exemplary complexes of the invention may comprise a targeting polypeptide and a nucleic acid binding moiety, encoded by a polypeptide comprising the amino acid sequence of SEQ ID NO: 2 or SEQ ID NO: 4.

In other certain examples, it is possible that the nucleic acid binding moiety and the targeting polypeptide are separated by a spacer peptide. Exemplary spacer peptides may comprise SEQ ID NO: 5 (SDGGGSGGGGSLE) or SEQ ID NO: 6: (DGGGSGGGGSL).

dsRNA with siRNA sequences that are complementary to the nucleotide sequence of the target gene are prepared. The siRNA nucleotide sequence is obtained from the siRNA Selection Program, Whitehead Institute for Biomedical Research, Massachusetts Institute of Technology, Cambridge, Mass. (jura.wi.mit.edu) after supplying the Accession Number or GI number from the National Center for Biotechnology Information website (ncvi.nlm.nih.gov). The Genome Database (gbd.org) provides the nucleic acid sequence link which is used as the National Center for Biotechnology Information accession number. Preparation of RNA to order is commercially available (Ambion Inc., Austin, Tex.; GenoMechanix, LLC, Gainesville, Fla.; and others). Determination of the appropriate sequences would be accomplished using the USPHS, NIH genetic sequence data bank. Alternatively, dsRNA containing appropriate siRNA sequences is ascertained using the strategy of Miyagishi and Taira (2003). DsRNA may be up to 800 base pairs long (Diallo M et al. 2003). The dsRNA optionally has a short hairpin structure (US Patent Application Publication 2004/0058886). Commercially available RNAi designer algorithms also exist (maidesigner.invitrogen.com/rnaiexpress/).

The invention features vectors that encode the complex as described herein. The vector can be any vector, for example, but not limited to a retroviral, adenoviral, adeno-associated viral, or lentiviral vector.

In certain preferred examples, the vector comprises a promoter suitable for expression in a mammalian cell.

Ligand-inhibitory nucleic acid binding complexes are prepared using existing plasmid technology (Caron et al. 2004; He et al. 2004). RNA binding proteins illustratively include histone (Jacobs and Imani 1988), RDE-4 (Tabara et al. 2002; Parrish and Fire 2001), and protamine (Warrant and Kim 1978). RNA binding protein cDNA is determined using the Gene Bank database (ncvi.nlm.nih.gov/IEB/Research/Acembly). For example, RDE-4 cDNA Gene Bank accession numbers are AY07926 and y1L832c2.3 (ncvi.nlm.nih.gov/IEB/Research/Acembly). RDE-4 initiates RNA interference by presenting dsRNA to Dicer (Tabara et al).

In certain examples, the suitability of the resulting ligand-dsRNA as a substrate for Dicer can be first determined in vitro using recombinant Dicer (Zhang H 2002, Provost 2002, Myers J W 2003). Optimal ligand molecule size and dsRNA length are thereby identified.

In certain preferred examples, the invention features pharmaceutical compositions for treating or preventing a disease or disorder in a subject comprising one or more inhibitory nucleic acids and a targeting polypeptide, wherein the targeting polypeptide consists of a cell surface receptor ligand, thereby treating or preventing a disease or disorder in a subject.

The pharmaceutical compositions, in certain embodiments, comprise treatment with an additional agent.

In other certain embodiment, the invention features a pharmaceutical composition for delivering one or more agents to a target cell comprising one or more inhibitory nucleic acids, wherein the one or more inhibitory nucleic acids are coupled to an agent, and a targeting polypeptide, wherein the targeting polypeptide consists of a cell surface receptor ligand, thereby treating or preventing a disease or disorder in a subject.

The agent can be, in certain examples, a therapeutic agent. Any therapeutic agent envisioned for use by the skilled practitioner is suitable for use in the instant invention. In preferred embodiments, the therapeutic agent is an anti-cancer compound. Examples of anti-cancer compounds include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodcpa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine, mechlorethamine oxide hydrochloride rethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, improsulfan, benzodepa, carboquone, triethylenemelamine, triethylenephosphoramide, triethylenethiophosphoramide, trimethylolomelamine, chlornaphazine, novembichin, phenesterine, trofosfamide, estermustine, chlorozotocin, gemzar, nimustine, ranimustine, dacarbazine, mannomustine, mitobronitol, aclacinomycins, actinomycin F(1), azaserine, bleomycin, carubicin, carzinophilin, chromomycin, daunorubicin, daunomycin, 6-diazo-5-oxo-1-norleucine, doxorubicin, olivomycin, plicamycin, porfiromycin, puromycin, tubercidin, zorubicin, denopterin, pteropterin, 6-mercaptopurine, ancitabine, 6-azauridine, carmofur, cytarabine, dideoxyuridine, enocitabine, pulmozyme, aceglatone, aldophosphamide glycoside, bestrabucil, defofamide, demecolcine, elfornithine, elliptinium acetate, etoglucid, flutamide, hydroxyurea, lentinan, phenamet, podophyllinic acid, 2-ethylhydrazide, razoxane, spirogemianium, tamoxifen, taxotere, tenuazonic acid, triaziquone, 2,2',2''-trichlorotriethylamine, urethan, vinblastine, vincristine, vindesine and related agents. 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspennine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cisporphyrin; cladribine; clomifene analogues; clotrimazole; collismycin A; collismycin B; combrctastatin A4; combrctastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; taxel; taxel analogues; taxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleo tides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred additional anti-cancer drugs are 5-fluorouracil and leucovorin. Additional cancer therapeutics include monoclonal antibodies such as rituximab, trastuzumab and cetuximab.

In other embodiments, the agent may be a toxin. For example, the toxin may be selected from, but not limited to the following: aplidin, azaribine, anastrozole, azacytidine, bleomycin, bortezomib, bryostatin-1, busulfan, calicheamycin, camptothecin, 10-hydroxycamptothecin, carmustine, celebrex, chlorambucil, cisplatin, irinotecan (CPT-11), SN-38, carboplatin, cladribine, cyclophosphamide, cytarabine, dacarbazine, docetaxel, dactinomycin, daunomycin glucuronide, daunorubicin, dexamethasone, diethylstilbestrol, doxorubicin, 2-pyrrolinodoxorubicine (2P-DOX), cyano-morpholino doxorubicin, doxorubicin glucuronide, epirubicin glucuronide, ethinyl estradiol, estramustine, etoposide, etoposide glucuronide, etoposide phosphate, floxuridine (FUdR), 3',5'-O-dioleoyl-FudR (FUdR-dO), fludarabine, flutamide, fluorouracil, fluoxymesterone, gemcitabine, hydroxyprogesterone caproate, hydroxyurea, idarubicin, ifosfamide, L-asparaginase, leucovorin, lomustine, mechlorethamine, medroprogesterone acetate, megestrol acetate, melphalan, mercaptopurine, 6-mercaptopurine, methotrexate, mitoxantrone, mithramycin, mitomycin, mitotane, phenyl butyrate, prednisone, procarbazine, paclitaxel, pentostatin, PSI-341, semustine streptozocin, tamoxifen, taxanes, taxol, testosterone propionate, thalidomide, thioguanine, thiotepa, teniposide, topotecan, uracil mustard, velcade, vinblastine, vinorelbine, vincristine, ricin, abrin, ribonuclease, onconase, rapLR1, DNase I, Staphylococcal enterotoxin-A, pokeweed antiviral protein, gelonin, diphtheria toxin, *Pseudomonas* exotoxin, *Pseudomonas* endotoxin and combinations thereof.

Other agents that can be used include anti-inflammatories.
Methods

The inventors of the instant application have developed novel compositions and methods for delivering inhibitory oligonucleotides to cells in a targeted and efficient manner. The compositions and methods are based on utilizing a cell surface receptor targeting ligand, for example a chemokine, and a domain that binds an inhibitory oligonucleotide, to efficiently deliver the inhibitory oligonucleotide to the cell that expresses the cell surface receptor targeting ligand. The invention provides advantages over prior methods in providing highly efficient and targeted complexes.

Accordingly, the invention features methods of silencing, or knocking down, gene expression in a cell using the complexes as described herein In certain examples, the invention features methods of silencing gene expression in a cell comprising contacting the cell with a complex comprising one or more inhibitory nucleic acids that reduce the expression of one or more target genes and a targeting polypeptide, wherein the targeting polypeptide comprises a cell surface receptor ligand, thereby silencing gene expression in the cell.

The invention also features methods of delivering inhibitory RNA molecules into a cell, where the methods comprise contacting the cell with a complex comprising one or more double stranded RNAs and a targeting polypeptide, wherein the targeting polypeptide comprises a cell surface receptor ligand, thereby delivering inhibitory RNA molecules into a cell.

The invention also features methods of treating or preventing a disease or disorder in a subject by silencing gene expression comprising: contacting the cell with a complex comprising one or more inhibitory nucleic acids that reduce the expression of one or more target genes and a targeting polypeptide, wherein the targeting polypeptide consists of a cell surface receptor ligand, thereby treating or preventing a disease or disorder in a subject.

In certain examples, the methods are used to treat cancer. In more particular examples, the complexes are useful in the claimed methods to treat leukemia.

Other cancers that may be treated include, but are not limited to:

Acute Lymphoblastic Leukemia, Acute Myeloid Leukemia, Adrenocortical Carcinoma, Basal Cell Carcinoma, Bladder Cancer, Bone Cancer, Brain Tumor, Breast Cancer, Cervical Cancer, Chronic Lymphocytic Leukemia, Chronic Myelogenous Leukemia, Chronic Myeloproliferative Disorders, Colon Cancer, Colorectal Cancer, Cutaneous T-Cell Lymphoma, Esophageal Cancer, Ewing Family of Tumors, Retinoblastoma, Gastric (Stomach) Cancer, Gastrointestinal Tumors, Glioma, Head and Neck Cancer, Hepatocellular (Liver) Cancer, Hodgkin Lymphoma, Islet Cell Tumors (Endocrine Pancreas), Kidney (Renal Cell) Cancer, Laryngeal Cancer, Lung Cancer, Non-Small Cell, Lung Cancer, Small Cell, Lymphoma, Medulloblastoma, Melanoma, Pancreatic Cancer, Prostate Cancer, Renal Cancer, Rectal cancer, Thyroid Cancer.

As described herein the methods can also comprise treatment with an additional agent.

In certain cases, the additional agent can be a therapeutic agent, as described herein.

The invention also features methods of delivering one or more agents to a target cell comprising contacting the cell with a complex comprising one or more inhibitory nucleic acids that reduce the expression of one or more target genes, wherein the one or more inhibitory nucleic acids are coupled to an agent, and a targeting polypeptide, wherein the targeting polypeptide consists of a cell surface receptor ligand, thereby delivering the agent to a target cell.

In other certain cases, the agent can be an imaging agent. Imaging agents can be used for diagnostic or prognostic purposes, and to determine the course of treatment.

Exemplary imaging agents include, but are not limited to, contrast media imaging agents, MRI CT contrast media, radiopharmaceuticals, x-ray contrast agents, cardiac imaging agents, technetium tc-99m, ultrasound contrast agent.

Thus, the invention features methods for delivering an imaging agent into a cell in a subject comprising contacting the cell with a complex comprising one or more inhibitory nucleic acids that reduce the expression of one or more target genes, wherein the one or more inhibitory nucleic acids are coupled to the imaging agent, and a targeting polypeptide, wherein the targeting polypeptide consists of a cell surface receptor ligand, delivering the agent into the cell.

In one embodiment, inhibitory nucleic acids, for example siNA molecules, of the invention are used as reagents in ex vivo applications. For example, siNA reagents are introduced into tissue or cells that are transplanted into a subject for therapeutic effect. The cells and/or tissue can be derived from an organism or subject that later receives the explant, or can be derived from another organism or subject prior to transplantation. The siNA molecules can be used to modulate the expression of one or more target genes in the cells or tissue, such that the cells or tissue obtain a desired phenotype or are able to perform a function when transplanted in vivo. In one embodiment, certain target cells from a patient are extracted. These extracted cells are contacted with siNAs targeting a specific nucleotide sequence within the cells under conditions suitable for uptake of the siNAs by these cells (e.g. using delivery reagents such as cationic lipids, liposomes and the like or using techniques such as electroporation to facilitate the delivery of siNAs into cells). The cells are then reintroduced back into the same patient or other patients. Thus, in one embodiment, the invention features a method of modulating the expression of a target gene in a tissue explant comprising: (a) synthesizing a complex of the invention, e.g. a complex comprising one or more inhibitory nucleic acids and a targeting polypeptide, wherein the targeting polypeptide consists of a cell surface receptor ligand, and wherein one of the siNA strands comprises a sequence complementary to RNA of the target gene; and (b) introducing the complex into a cell of the tissue explant derived from a particular organism under conditions suitable to modulate the expression of the target gene in the tissue explant. In another embodiment, the method further comprises introducing the tissue explant back into the organism the tissue was derived from or into another organism under conditions suitable to modulate the expression of the target gene in that organism.

In certain examples, the cell is a cultured cell. In other certain examples, the cell is part of a subject animal. The cell can be selected from, but is not limited to, immune cells, epithelial cells, endothelial cells, cardiac cells, neural cells, hepatocytes, lymphocytes and myocytes.

The cell can be a malignant cell.

The cell can be a stem cell.

The subject can be a mammal, and in certain preferred embodiments, the subject is a human. In certain embodiments, the subject is suffering from an immunological disease or disorder, a neoplasia of hyperfroliferative disease or disorder.

A major goal of treatment of neoplastic diseases and hyperproliferative disorders is to ablate the abnormally growing cells while leaving normal cells untouched. Various methods are under development for providing treatment, but none provide the requisite degree of specificity. The methods as described herein, using a complex comprising one or more inhibitory nucleic acids and a targeting polypeptide, wherein the targeting polypeptide consists of a cell surface receptor ligand, provide enhanced targeting and specificity for the treatment of diseases, for example neoplastic diseases, immunological diseases, and hyperproliferative disorders.

In certain cases, the methods of the invention are used to diagnose a metastasis.

The use of the method for the treatment of cancer or proliferative diseases is preferred in certain embodiments. The delivery of compounds to specific cell types, for example, cancer cells, can be accomplished by utilizing receptors associated with specific cell types. Particular receptors are overexpressed in certain cancerous cells, including the high affinity folic acid receptor. For example, the high affinity folate receptor is a tumor marker that is overexpressed in a variety of neoplastic tissues, including breast, ovarian, cervical, colorectal, renal, and nasopharyngeal tumors, but is expressed to a very limited extent in normal tissues. The use of folic acid based conjugates to transport exogenous compounds across cell membranes can provide a targeted delivery approach to the treatment and diagnosis of disease and can provide a reduction in the required dose of therapeutic compounds. Furthermore, therapeutic bioavailability, pharmacodynamics, and pharmacokinetic parameters can be modulated through the use of bioconjugates, including folate bioconjugates. Godwin et al., 1972, J. Biol. Chem., 247, 2266-2271, report the synthesis of biologically active pteroyloligo-L-glutamates. Habus et al., 1998, Bioconjugate Chem., 9, 283-291, describe a method for the solid phase synthesis of certain oligonucleotide-folate conjugates. Cook, U.S. Pat. No. 6,721,208, describes certain oligonucleotides modified with specific conjugate groups. The use of biotin and folate conjugates to enhance transmembrane transport of exogenous molecules, including specific oligonucleotides has been reported by Low et al., U.S. Pat. Nos. 5,416,016, 5,108,921, and International PCT publication No. WO 90/12096. Manoharan et al., International PCT publication No. WO 99/66063 describe certain folate conjugates, including specific nucleic acid folate conjugates with a phosphoramidite moiety attached to the nucleic acid component of the conjugate, and methods for the synthesis of these folate conjugates. Nomura et al., 2000, J. Org. Chem., 65, 5016-5021, describe the synthesis of an intermediate, alpha-[2-(trimethylsilyl)ethoxycarbonl] folic acid, useful in the synthesis of certain types of folate-nucleoside conjugates. Guzaev et al., U.S. Pat. No. 6,335,434, describes the synthesis of certain folate oligonucleotide conjugates.

Dosage and Administration

The compositions of the invention may be administered systemically. As used herein, the term "systemic administration" is meant to include in vivo systemic absorption or accumulation of drugs in the blood stream followed by distribution throughout the entire body. Administration routes which lead to systemic absorption include, without limitation: intravenous, subcutaneous, intraperitoneal, intranasal, inhalation, oral, intrapulmonary and intramuscular. Each of these administration routes expose the desired negatively charged polymers, for example, nucleic acids, to an accessible diseased tissue. The rate of entry of a drug into the circulation has been shown to be a function of molecular weight or size.

The compositions of the invention can be administered to cells by a variety of methods known to those of skill in the art, including, but not restricted to, encapsulation in liposomes; by iontophoresis; or by incorporation into other vehicles, such as hydrogels, cyclodextrins, biodegradable nanocapsules, and bioadhesive microspheres; or by proteinaceous vectors (O'Hare and Normand, International PCT Publication No. WO 00/53722). Alternatively, the nucleic acid/vehicle combination may be locally delivered by direct injection or by use of an infusion pump. Direct injection of the complexes of the invention, whether subcutaneous, intramuscular, or intradermal, can take place using standard needle and syringe methodologies, or by needle-free technologies such as those described in Conry, et al., Clin. Cancer Res. 5:2330-2337, 1999, and Barry, et al., International PCT Publication No. WO 99/31262.

The invention also features the use of the composition comprising surface-modified liposomes containing poly (ethylene glycol) lipids (PEG-modified, or long-circulating liposomes or stealth liposomes). These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug. Lasic, et al., Chem. Rev. 95:2601-2627, 1995; Ishiwata, et al., Chem. Pharm. Bull. 43:1005-1011, 1995. Such liposomes have been shown to accumulate selectively in tumors, presumably by extravasation and capture in the neovascularized target tissues. Lasic, et al., Science 267:1275-1276, 1995; Oku, et al., Biochim. Biophys. Acta 1238:86-90, 1995. The long-circulating liposomes enhance the pharmacokinetics and pharmacodynamics of DNA and RNA, particularly compared to conventional cationic liposomes which are known to accumulate in tissues of the MPS. Liu, et al., J. Biol. Chem. 42:24864-24870, 1995; Choi, et al., International PCT Publication No. WO 96/10391; Ansell, et al., International PCT Publication No. WO 96/10390; and Holland, et al., International PCT Publication No. WO 96/10392. Long-circulating liposomes are also likely to protect drugs from nuclease degradation to a greater extent compared to cationic liposomes, nucleotided on their ability to avoid accumulation in metabolically aggressive MPS tissues such as the liver and spleen.

The present disclosure also includes compositions prepared for storage or administration, which include a pharmaceutically effective amount of the desired compounds in a pharmaceutically acceptable carrier or diluent. Acceptable carriers or diluents for therapeutic use are well known in the pharmaceutical art, and are described, for example, in Remington's Pharmaceutical Sciences, Mack Publishing Co., A. R. Gennaro ed., 1985. For example, preservatives, stabilizers, dyes and flavoring agents may be provided. These include sodium benzoate, sorbic acid and esters of p-hydroxybenzoic acid. In addition, antioxidants and suspending agents may be used.

A pharmaceutically effective dose is that dose required to prevent, inhibit the occurrence of, or treat (alleviate a symptom to some extent, preferably all of the symptoms) a disease state. In certain examples, the disease state may be cancer. The pharmaceutically effective dose depends on the type of disease, the composition used, the route of administration, the type of mammal being treated, the physical characteristics of the specific mammal under consideration, concurrent medication, and other factors that those skilled in the medical arts will recognize. Generally, an amount between 0.1 mg/kg and 100 mg/kg body weight/day of active ingredients is administered dependent upon potency of the negatively charged polymer.

Patient Monitoring

The disease state or treatment of a patient having a disease or disorder, for example a neoplasia, can be monitored using the methods and compositions of the invention.

In one embodiment, the tumor progression of a patient can be monitored using the methods and compositions of the invention. Such monitoring may be useful, for example, in assessing the efficacy of a particular drug in a patient. For examples, therapeutics that alter the expression of a target polypeptide that is overexpressed in a neoplasia are taken as particularly useful in the invention.

Kits

The invention also provides kits for treating or preventing a disease or disorder in a subject by silencing gene expression. In preferred examples, the kits provide one or more inhibitory nucleic acids and a targeting polypeptide, wherein the targeting polypeptide consists of a cell surface receptor ligand. In other preferred examples, the kits comprise the fusion molecule as described herein, and instructions for use.

In other embodiments, the kit comprises a sterile container which contains the inhibitory nucleotide, the targeting polypeptide and optionally additional agents; such containers can be boxes, ampules, bottles, vials, tubes, bags, pouches, blister-packs, or other suitable container form known in the art. Such containers can be made of plastic, glass, laminated paper, metal foil, or other materials suitable for holding nucleic acids. The instructions will generally include information about the use of the inhibitory nucleotides and additional agents as described herein and their use in the methods as described herein. Preferably, the kit further comprises any one or more of the reagents described in the diagnostic assays described herein. In other embodiments, the instructions include at least one of the following: description of the inhibitory nucleotides; methods for using the enclosed materials for the diagnostic and prognostic methods as described herein; precautions; warnings; indications; clinical or research studies; and/or references. The instructions may be printed directly on the container (when present), or as a label applied to the container, or as a separate sheet, pamphlet, card, or folder supplied in or with the container.

EXAMPLES

It is hypothesized that ligands that target cell surface receptors, for example chemokines, might be utilized to deliver inhibitory nucleotides, for example siRNA. Advantageously, this would enable the utilization of inhibitory nucleotides linked to ligands that target cell surface receptors that are differentially expressed on certain cells, in a method to target specific cells. For example, chemokine receptors are differentially expressed on certain cells, including tumors. Reported herein is the development of a novel composition that can efficiently deliver inhibitory nucleotides to cells that express certain receptors. In certain preferred aspects, the composition comprises a complex comprising one or more inhibitory nucleic acids and a targeting polypeptide, wherein the targeting polypeptide consists of a cell surface receptor ligand. In exemplary embodiments, the novel compositions efficiently deliver siRNA to cells that express respective chemokine receptors.

The technology is very simple, as the compositions specifically associate siRNA in saline without any additional manipulations. Thus, a single complex can be utilized for delivering of various siRNA. However, the complex can be also utilized after permanent cross-linking with siRNA, if needed. Moreover, the complex can also deliver oligonucleotides and siRNA that are labeled with various fluorochromes. Thus, this technology would enable the use of the complexes as described herein for diagnostic purposes both in vitro and in vivo, for example, to trace or localize various cells and to determine tumor metastasis and aberrant proliferation or homing of immune cells. The complexes can deliver siRNA to tumor cells or various aberrantly functioning immune cells to combat cancers and autoimmunity.

This invention is further illustrated by the following examples, which should not be construed as limiting. All documents mentioned herein are incorporated herein by reference.

Example 1

The invention features, generally, complexes comprising one or more inhibitory nucleic acids and a targeting polypeptide, where the targeting polypeptide consists of a cell surface receptor ligand.

In FIG. 1, the complex that targets the chemokine CCR4 is referred to as TARC-ARP. TARC is an abbreviation for thymus- and activation-regulated chemokine. Thus, the TARC-ARP can deliver an inhibitory nucleotide, in this case, siRNA against the chemokine TARC/CCL17, abbreviated as siTARC.

Figure 1B:
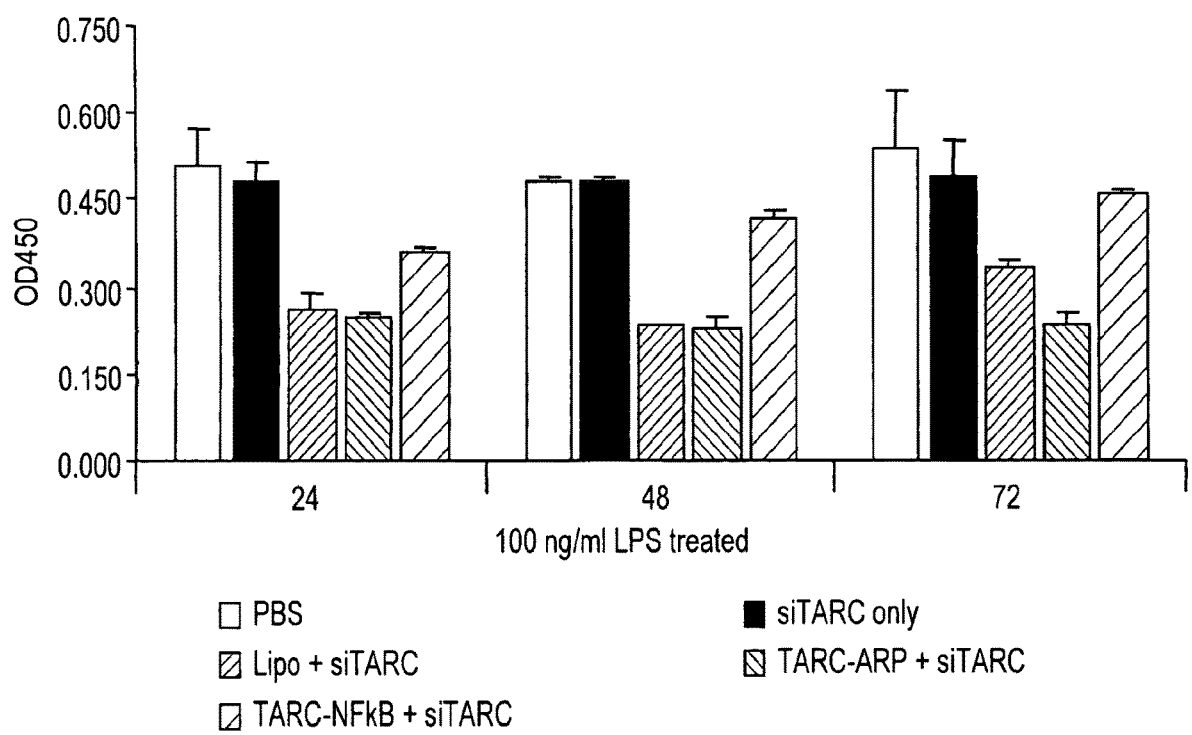

FIG. 1A and FIG. 1B demonstrate that the complex that targets chemokine CCR4 (TARC-ARP) can deliver siRNA against chemokine TARC/CCL17 (siTARC) and efficiently abrogate production/secretion of TARC/CCL17 from breast cancer 4T1 cells. The 4T1 cells express both TARC and its chemokine receptor CCR4. The efficiency of the complex-mediated gene "silencing" was comparable with lipofectin-mediated transfection techniques (Lipo+siTARC). In contrast, no gene silencing was detected when siRNA alone (siTARC) or siTARC mixed with control TARC (TARC-NFkB that does not have siRNA binding sites) were used. The cells were tested at various times post siRNA delivery without (FIG. 1A) or with LPS activation (FIG. 1B).

Figure 1C:
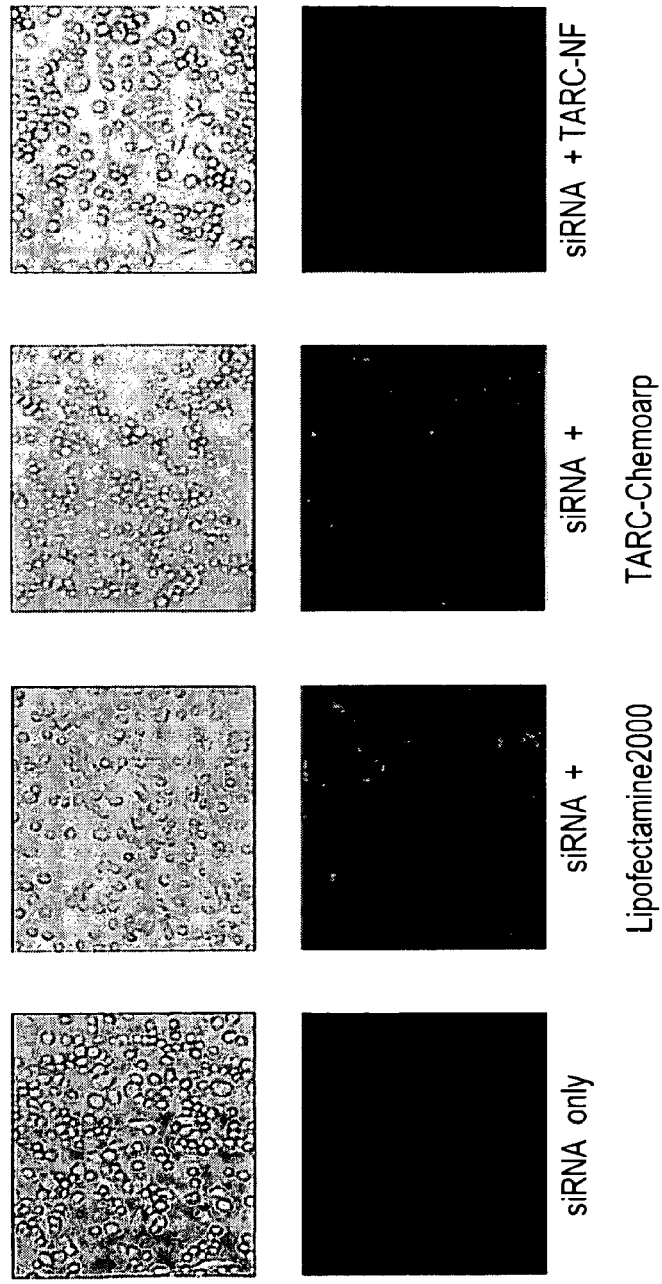

FIG. 1C shows TARC-ARP can efficiently deliver siRNA to breast cancer cells that express CCR4. TARC-complex or control TARC-NF proteins (1 mop were mixed with Alexa-488-labelled siRNA (20 pmol) in saline for 30 min at room temperature prior to adding to cells. Control cells also were incubated with Alexa-488-labelled siRNA (20 pmol) or transfected with siRNA using Lipofectamine-2000 (Invitrogen). After 24 hours of incubation, the cells were analyzed under visualized light (top panel) or under 555 nm wavelength excitation.

Example 2

The DNA sequence of a complex that contains TARC fused with protamine fragment is described in FIG. 2 and shown in SEQ ID NO: 1, below.

```
                                              SEQ ID NO: 1
ATGGCACGAGGGACCAACGTGGGCCGGGAGTGCTGCCTGGAGTACTTCAA

GGGAGCCATTCCCCTTAGAAAGCTGAAGACGTGGTACCAGACATCTGAGG

ACTGCTCCAGGGATGCCATCGTTTTTGTAACTGTGCAGGGCAGGGCCATC

TGTTCGGACCCCAACAACAAGAGAGTGAAGAATGCAGTTAAATACCTGCA

AAGCCTTGAGAGGTCTGATGGTGGTGGCTCTGGCGGTGGGGGTAGCCTCG

ACCGCAGCCAGAGCCGTAGCCGTTATTACCGCCAGCGCCAACGTTCTCGC

CGCCGTCGCCGTCGCAGCCTCGAGCGTGGATCCGCAGAAGAACAGAAACT

GATCTCAGAAGAGGATCTGGCCCACCACCATCACCATCACTAA
```

The protein sequence of the complex that contains TARC associated with protamine fragment is shown below in FIG. 2 and in SEQ ID NO: 2. In SEQ ID NO: 2 the mature sequence of human TARC/CCL17 contains Met (Italic, underlined) and protamine fragment (Italic). The spacer peptide fragment (underlined small letters) used to separate chemokine from protamine. The construct also contains c-myc-tag and six His residues for analytical use and protein purification purposes. It is of note that the c-myc-tag and six His residues are not necessary, and some constructs do not have them.

```
                                              SEQ ID NO: 2
MARGTNVGRECCLEYFKGAIPLRKLKTWYQTSEDCSRDAIVFVTVQGRAI

CSDPNNKRVKNAVKYLQSLERS DGGGSGGGGSL

DRSQSRSRYYRQRQRSRRRRRRSLERGSAEEQKLISEEDLAHHHHHH.
```

The DNA sequence of a complex that contains TARC associated with RNA binding domain of HBAg is described in FIG. 3 and shown in SEQ ID NO: 3, below.

SEQ ID NO: 3
ATCGCACGAGGGACCAACGTGGGCCGCCACTCCTGCCTGGAGTACTTCAA

GGGAGCCATTCCCCTTAGAAAGCTGAAGACGTGGTACCAGACATCTGAGG

ACTGCTCCAGGGATGCCATCGTTTTTGTAACTGTGCAGGGCAGGGCCATC

TGTTCGGACCCCAACAACAAGAGAGTGAAGAATGCAGTTAAATACCTGCA

AAGCCTTGAGAGGTCTGATGGTGGTGGCTCTGGCGGTGGGGGTAGCctcg agAGACGACGAGGCAGGtCcCCtAgAAGAAGAACTCCCTCgCCTCgcAGA CGAAGGTCTCAATCGCCGCGTCGCAgAAgATCTCAATCTCGGGTCGACCA CCaTCACCATCaCTAA The protein sequence of the complex that contains TARC associated with RNA binding domain of HBcAg is shown in FIG. 3, and in SEQ ID NO: 4, below. Mature sequence of human TARC/CCL17 that contains Met (Italic, underlined) and RNA binding domain of HBcAg (Italic). The spacer peptide fragment (underlined small letters) used to separate chemokine from RNA binding domain of HBcAg. The construct also contains five His residues for analytical use and protein purification purposes. It is of note that the five His residues are not necessary, some constructs do not have them.

SEQ ID NO: 4
*M* RGTNVGRECCLEYFKGAIPLRKLKTWYQTSEDCSRDAIVFVT

VQGRAICSDPNNKRVKNAVKYLQSLER SDGGGSGGGGSLE

*RRRGRSPRRRTPSPRRRRSQSPRRRRSQSRVD* HHHHH

In other examples, the complexes are modified. For example, the RNA binding portion of the complex is modified by reducing its size and/or increasing affinity. As described herein, His residues may be included in the constructs for analytical use and protein purification purposes; however these His residues are not necessary. Accordingly, certain constructs do not have His-tag. The exclusion of the His tag allows increased RNA binding affinity of the complex.

The protein sequence of the complex that contains TARC-Arp, human TARC/CCL17 fused with a hypothetical RNA-binding domain of HBV virus, is shown in FIG. 5, and in SEQ ID NO: 9, below. In certain embodiments the complex is used to deliver, for example, oligonucleotides and miRNA/siRNA to CCR-4 expressing cells. A spacer sequence (GGGSGGG; SEQ ID NO: 7) was inserted between TARC/CCL17 and the hypothetical RNA-binding domain of HBV virus.

In certain preferred embodiments, TARC-Arp is used to knock off gene expression by targeting CCR-4 expressing CD4 T cells and regulatory T cells in allergic pulmonary diseases.

SEQ ID NO: 9
ARGTNVGRECCLEYFKGAIPLRKLKTWYQTSEDCSRDAIVFVTVQGRAIC

SDPNNKRVKNAVKYLQSLERSD*GGGSGGGGS*SPGRRRRRSQSRRRRR

The protein sequence of the complex that contains RANTES-Arp, RANTES/CCL5 fused with a hypothetical RNA-binding domain of HBV virus, is shown in FIG. 5 and in SEQ ID NO: 10, shown below. In certain embodiments the complex is used to deliver, for example, oligonucleotides and miRNA/siRNA to CCR5-expressing cells. A spacer sequence (GGGSGGG; SEQ ID NO: 7) was inserted between RANTES and the hypothetical RNA-binding domain of HBV virus.

In certain preferred embodiments, RANTES-Arp will be tested for inactivation of HIV genes in infected CD4 T cells.

SEQ ID NO: 10
SPYSSDTTPCCFAYIARPLPRAHIKEYFYTSGKCSNPAVVFVTRKNRQVC

ANPEKKWVREYINSLEMS*GGGSGGGGS*SPGRRRRRSQSRRRRR

The protein sequence of the complex that contains MCP1-Arp, human MCP1/CCL2 fused with a hypothetical RNA-binding domain of HBV virus, is shown in FIG. 5 and SEQ ID NO: 11. In certain embodiments the complex is used to deliver, for example, oligonucleotides and miRNA/siRNA to CCR2-expressing cells. A spacer sequence (GGGGSGGG; SEQ ID NO: 8) was inserted between MCP-1 and the hypothetical RNA-binding domain of HBV virus.

In certain preferred embodiments, MCP1-Arp will be tested for inactivation of immunomodulatory genes expressed by M2 macrophages to combat cancer progression and metastasis:

SEQ ID NO: 11
EAPDAINAPVTCCYNFTNRKISVQRLASYRRITSSKCPKEAVIFKTIVAK

EICADPKQKWVQDSMDHLDKQTQTPKT*GGGGSGGGGS*PGRRRRRSQSRRR

RR

Example 3: Antisense Oligomer to Interleukin-10 (IL-10) Inhibits IL-10 Expression Experiments were also performed with antisense oligomers to interleukin-10 (IL-10) as part of complexes as described herein. In the same type of experiments as described above, it was found that antisense oligomers to IL-10 in a complex as described herein are effective to inhibit IL-10 expression.

Figure 6:
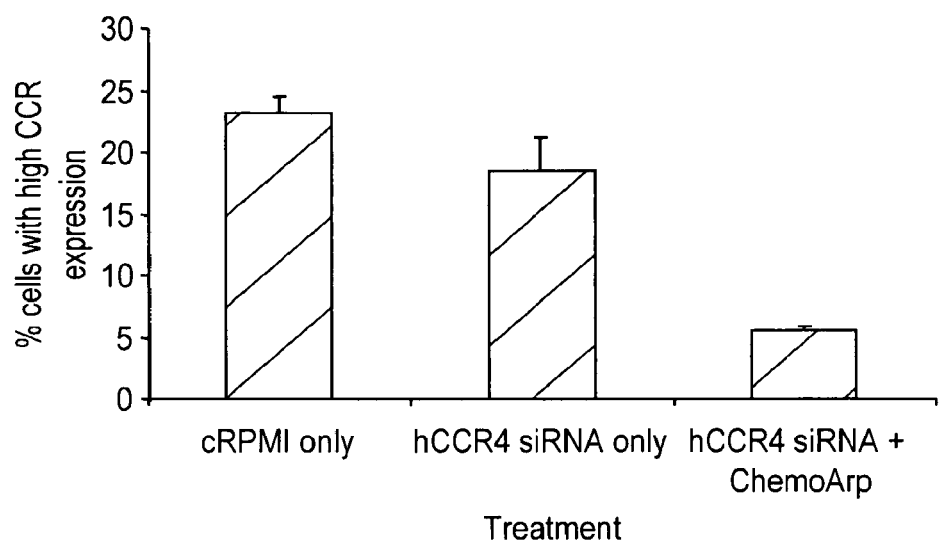
FIG. 6 shows results of experiments showing TARC-ARP knocks down CCR4 expression on human T Cell tumor cells

Example 4: siRNA Knock Down siRNA knockdown experiments were performed. CCR4 expression is also expressed by human T cell leukemia and ATLL and is associated with a poor outcome of the disease. As shown in FIG. 6, siRNA was delivered to inactivate CCR4 expression in human T cell tumors using TARC-Arp, as described above.

Figure 7:
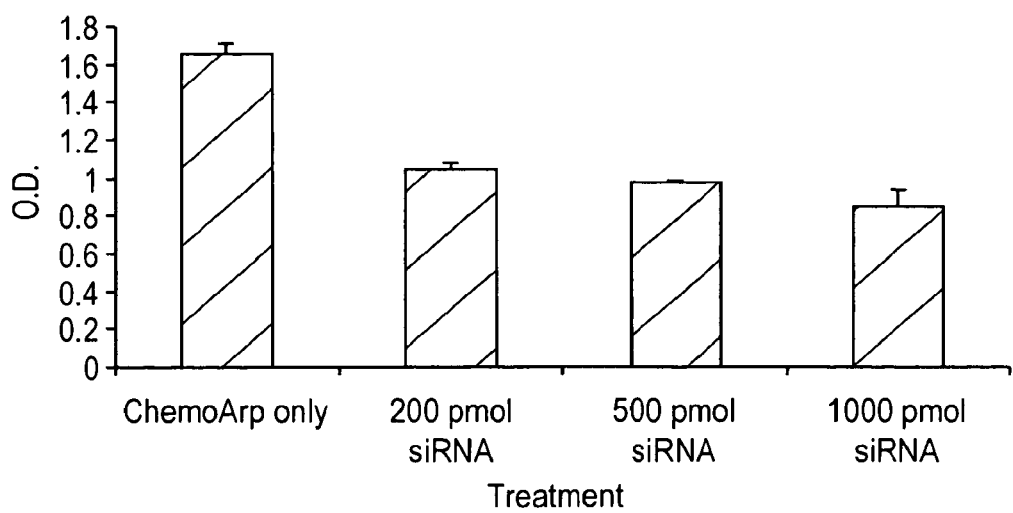
FIG. 7 is a graph that shows TARC-ARP can transiently inhibit IL-6 expression by tumor cells.

IL-6 is regulatory cytokine which is involved in various human diseases and cancer. Tumors are known to express IL-6 to escape from immunosurveillance. FIG. 7 demonstrates that IL-6 expression can be abrogated in breast cells by delivering siRNA against IL-6 using TARC-Arp.

Suitably, using the methods described, complexes will be produced that target every chemokine receptor, thus allowing use of the complexes for the inactivation of genes of interest, for example, but not only limited to, cytokines and signaling molecules; genes of intracellular pathogens, such as HW, HCV, or TB, *salmonella* and etc. Such a strategy would has clinical implications in treating and preventing cancer, autoimmune diseases, and chronic infection. In addition, the complexes described herein are suitably used as research tools, as they are can efficiently transduce primary cells with siRNA.

Example 5: Production

In certain examples, the production of the complex has been modified for yeast in order to produce efficient secretion from yeast. As a result, this allows for a simplified production and increased yield.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A fusion molecule comprising a targeting polypeptide, and a nucleic acid binding domain, wherein the targeting, polypeptide is selected from monocyte chemoattractant protein 1 (MCP-1/CCL-2), thymus- and activation-regulated chemokine (TARC/CCL17), Regulation upon Activation Normal T cell Express Sequence (RANTES/CCL5), and a receptor binding fragment of MCP-1, TARC, or RANTES, and the nucleic acid binding domain is amino acids 87 through 102 of SEQ ID NO: 11.

2. The fusion molecule of claim 1, wherein the fusion molecule includes one or more inhibitory nucleic acids thereby forming an inhibitory nucleic acid-fusion molecule complex.

3. The fusion molecule of claim 1, wherein the targeting polypeptide is MCP-1 or a receptor binding fragment thereof with an amino acid sequence that is amino acids 3 through 77 of SEQ ID NO: 11.

4. The fusion molecule of claim 1, wherein the targeting polypeptide is TARC or a receptor binding fragment thereof with an amino acid sequence that is amino acids 1 through 72 of SEQ ID NO: 9.

5. The fusion molecule of claim 1, wherein the targeting polypeptide is RANTES or a receptor binding fragment thereof with an amino acid sequence that is amino acids 1 through 68 of SEQ ID NO: 10.

6. The fusion molecule of claim 1, wherein the fusion molecule comprises a spacer sequence in between the targeting polypeptide and nucleic acid binding domain.

7. The fusion molecule of claim 6, wherein the spacer peptide comprises an amino acid sequence selected from the group consisting of SEQ ID NO: 5 (SDGGGSGGGGSLE), SEQ ID NO: 6 (DGGGSGGGGSL), SEQ ID NO: 7 (GGGSGGGG), and SEQ ID NO: 8 (GGGGSGGGG).

8. The fusion molecule of claim 2, wherein the inhibitory nucleic acid is selected from the group consisting of antisense nucleic acid, short interfering nucleic acid (siNA), short interfering RNA (siRNA), double-stranded RNA (dsRNA), micro-RNA (miRNA), short hairpin RNA (shRNA) and combinations thereof.

9. The fusion molecule of claim 8, wherein the inhibitory nucleic acid comprises a modified nucleotide.

10. The fusion molecule of claim 8, wherein the inhibitory nucleic acid hybridizes to or is complementary to a nucleic acid that encodes a cytokine.

11. The fusion molecule of claim 8, wherein the inhibitory nucleic acid hybridizes to or is complementary to a nucleic acid that encodes a chemokine.

12. The fusion molecule of claim 10, wherein the inhibitory nucleic acid hybridizes to or is complementary to a nucleic acid that encodes IL-10.

13. A fusion molecule comprising the amino acid sequence of SEQ ID NO: 11.

14. A complex comprising an inhibitory nucleic acid and the fusion molecule of claim 1, wherein the fusion molecule comprises the amino acid sequence of SEQ ID NO: 11.

15. The complex of claim 14, wherein the inhibitory nucleic acid is selected from the group consisting of antisense nucleic acid, short interfering nucleic acid (siNA), short interfering RNA (siRNA), double-stranded RNA (dsRNA), micro-RNA (miRNA), short hairpin RNA (shRNA) and combinations thereof.

16. The complex of claim 15, wherein the inhibitory nucleic acid hybridizes to or is complementary to a nucleic acid that encodes IL-10.

17. A fusion molecule comprising the amino acid sequence of SEQ ID NO: 9.

18. A fusion molecule comprising the amino acid sequence of SEQ ID NO: 10.

* * * * *

SEQUENCE LISTING

```
<160> NUMBER OF SEQ ID NOS: 14

<210> SEQ ID NO 1
<211> LENGTH: 393
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 1
atggcacgag ggaccaacgt gggccgggag tgctgcctgg agtacttcaa gggagccatt      60
ccccttagaa agctgaagac gtggtaccag acatctgagg actgctccag ggatgccatc     120
gtttttgtaa ctgtgcaggg cagggccatc tgttcggacc ccaacaacaa gagagtgaag     180
aatgcagtta aatacctgca aagccttgag aggtctgatg gtggtggctc tggcggtggg     240
ggtagcctcg accgcagcca gagccgtagc cgttattacc gccagcgcca acgttctcgc     300
cgccgtcgcc gtcgcagcct cgagcgtgga tccgcagaag aacagaaact gatctcagaa     360
gaggatctgg cccaccacca tcaccatcac taa                                  393

<210> SEQ ID NO 2
<211> LENGTH: 130
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Met Ala Arg Gly Thr Asn Val Gly Arg Glu Cys Cys Leu Glu Tyr Phe
1               5                   10                  15

Lys Gly Ala Ile Pro Leu Arg Lys Leu Lys Thr Trp Tyr Gln Thr Ser
            20                  25                  30

Glu Asp Cys Ser Arg Asp Ala Ile Val Phe Val Thr Val Gln Gly Arg
        35                  40                  45

Ala Ile Cys Ser Asp Pro Asn Asn Lys Arg Val Lys Asn Ala Val Lys
    50                  55                  60

Tyr Leu Gln Ser Leu Glu Arg Ser Asp Gly Gly Gly Ser Gly Gly Gly
65                  70                  75                  80

Gly Ser Leu Asp Arg Ser Gln Ser Arg Ser Arg Tyr Tyr Arg Gln Arg
                85                  90                  95

Gln Arg Ser Arg Arg Arg Arg Arg Ser Leu Glu Arg Gly Ser Ala
            100                 105                 110
```

Glu Gln Lys Leu Ile Ser Glu Glu Asp Leu Ala His His His His
    115                 120                 125

His His
    130

<210> SEQ ID NO 3
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 3
atggcacgag ggaccaacgt gggccgggag tgctgcctgg agtacttcaa gggagccatt      60 cccctttagaa agctgaagac gtggtaccag acatctgagg actgctccag ggatgccatc    120
gtttttgtaa ctgtgcaggg cagggccatc tgttcggacc ccaacaacaa gagagtgaag    180
aatgcagtta aatacctgca aagccttgag aggtctgatg gtggtggctc tggcggtggg    240
ggtagcctcg agagacgacg aggcaggtcc cctagaagaa gaactccctc gcctcgcaga    300
cgaaggtctc aatcgccgcg tcgcagaaga tctcaatctc gggtcgacca ccatcaccat    360
cactaa                                                                366

<210> SEQ ID NO 4
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Met Arg Gly Thr Asn Val Gly Arg Glu Cys Cys Leu Glu Tyr Phe Lys
1               5                   10                  15

Gly Ala Ile Pro Leu Arg Lys Leu Lys Thr Trp Tyr Gln Thr Ser Glu
            20                  25                  30

Asp Cys Ser Arg Asp Ala Ile Val Phe Val Thr Val Gln Gly Arg Ala
        35                  40                  45

Ile Cys Ser Asp Pro Asn Asn Lys Arg Val Lys Asn Ala Val Lys Tyr
    50                  55                  60

Leu Gln Ser Leu Glu Arg Ser Asp Gly Gly Ser Gly Gly Gly
65                  70                  75                  80

Ser Leu Glu Arg Arg Arg Gly Arg Ser Pro Arg Arg Thr Pro Ser
                85                  90                  95

Pro Arg Arg Arg Ser Gln Ser Pro Arg Arg Arg Ser Gln Ser
            100                 105                 110

Arg Val Asp His His His His
        115                 120

<210> SEQ ID NO 5
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 5

Ser Asp Gly Gly Gly Ser Gly Gly Gly Ser Leu Glu
1               5                   10

<210> SEQ ID NO 6
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Asp Gly Gly Gly Ser Gly Gly Gly Ser Leu
1               5                   10

<210> SEQ ID NO 7
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Gly Gly Gly Ser Gly Gly Gly Gly
1               5

<210> SEQ ID NO 8
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Gly Gly Gly Gly Ser Gly Gly Gly Gly
1               5

<210> SEQ ID NO 9
<211> LENGTH: 96
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Ala Arg Gly Thr Asn Val Gly Arg Glu Cys Cys Leu Glu Tyr Phe Lys
1               5                   10                  15

Gly Ala Ile Pro Leu Arg Lys Leu Lys Thr Trp Tyr Gln Thr Ser Glu
            20                  25                  30

Asp Cys Ser Arg Asp Ala Ile Val Phe Val Thr Val Gln Gly Arg Ala
        35                  40                  45

Ile Cys Ser Asp Pro Asn Asn Lys Arg Val Lys Asn Ala Val Lys Tyr
    50                  55                  60

Leu Gln Ser Leu Glu Arg Ser Asp Gly Gly Ser Gly Gly Gly Gly
65                  70                  75                  80

Ser Pro Gly Arg Arg Arg Arg Ser Gln Ser Arg Arg Arg Arg
            85                  90                  95
```

```
<210> SEQ ID NO 10
<211> LENGTH: 92
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
            20                  25                  30

Lys Cys Ser Asn Pro Ala Val Val Phe Val Thr Arg Lys Asn Arg Gln
        35                  40                  45

Val Cys Ala Asn Pro Glu Lys Lys Trp Val Arg Glu Tyr Ile Asn Ser
    50                  55                  60

Leu Glu Met Ser Gly Gly Gly Ser Gly Gly Gly Ser Pro Gly Arg
65                  70                  75                  80

Arg Arg Arg Ser Gln Ser Arg Arg Arg Arg
            85                  90

<210> SEQ ID NO 11
<211> LENGTH: 102
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Glu Ala Pro Asp Ala Ile Asn Ala Pro Val Thr Cys Cys Tyr Asn Phe
1               5                   10                  15

Thr Asn Arg Lys Ile Ser Val Gln Arg Leu Ala Ser Tyr Arg Arg Ile
            20                  25                  30

Thr Ser Ser Lys Cys Pro Lys Glu Ala Val Ile Phe Lys Thr Ile Val
        35                  40                  45

Ala Lys Glu Ile Cys Ala Asp Pro Lys Gln Lys Trp Val Gln Asp Ser
    50                  55                  60

Met Asp His Leu Asp Lys Gln Thr Gln Thr Pro Lys Thr Gly Gly Gly
65                  70                  75                  80

Gly Ser Gly Gly Gly Gly Ser Pro Gly Arg Arg Arg Arg Ser Gln
            85                  90                  95

Ser Arg Arg Arg Arg
            100

<210> SEQ ID NO 12
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 12

His His His His His His
1               5
```

-continued

```
<210> SEQ ID NO 13
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 5xHis tag"

<400> SEQUENCE: 13

His His His His His
1               5

<210> SEQ ID NO 14
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: Any amino acid

<400> SEQUENCE: 14

Trp Ser Xaa Trp Ser
1               5
```